United States Patent
Akatsu et al.

(10) Patent No.: US 10,888,279 B2
(45) Date of Patent: Jan. 12, 2021

(54) BIOMETRIC INFORMATION MONITORING SYSTEM

(71) Applicants: MINEBEA MITSUMI Inc., Nagano (JP); NATIONAL UNIVERSITY CORPORATION CHIBA UNIVERSITY, Chiba (JP)

(72) Inventors: Hiroyuki Akatsu, Tokyo (JP); Kunihiko Sato, Fujisawa (JP); Norihito Iida, Sagamihara (JP); Shiroh Isono, Chiba (JP)

(73) Assignees: MINEBEA MITSUMI INC., Nagano (JP); NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 0 days.

(21) Appl. No.: 15/936,676

(22) Filed: Mar. 27, 2018

(65) Prior Publication Data
US 2018/0206793 A1  Jul. 26, 2018

Related U.S. Application Data

(63) Continuation of application No. PCT/JP2016/004342, filed on Sep. 26, 2016.

(30) Foreign Application Priority Data

Sep. 29, 2015  (JP) ................... 2015-191959
Oct. 27, 2015  (JP) ................... 2015-210444

(51) Int. Cl.
*A61B 5/00*  (2006.01)
*A61B 5/08*  (2006.01)
(Continued)

(52) U.S. Cl.
CPC .......... *A61B 5/6892* (2013.01); *A61B 5/0205* (2013.01); *A61B 5/0255* (2013.01);
(Continued)

(58) Field of Classification Search
CPC ... A61B 5/6892; A61B 5/0205; A61B 5/0816; A61B 5/113; A61B 5/4809;
(Continued)

(56) References Cited

U.S. PATENT DOCUMENTS

| | | | |
|---|---|---|---|
| 2005/0273940 A1* | 12/2005 | Petrosenko | A61B 5/1126 5/722 |
| 2007/0010743 A1 | 1/2007 | Arai | |

(Continued)

FOREIGN PATENT DOCUMENTS

| | | |
|---|---|---|
| CN | 102113034 A | 6/2011 |
| JP | 5392577 A | 8/1978 |

(Continued)

OTHER PUBLICATIONS

Brinks, Mark; Muller, Christopher; Schierz, Christoph, "Contact-free measurement of heart rate, respiration rate, and body movements during sleep" 2006 Behavior Research Methods, 38 (3), 511-521.*

(Continued)

*Primary Examiner* — Lynsey C Eiseman
*Assistant Examiner* — Jessandra F Hough
(74) *Attorney, Agent, or Firm* — Pearne & Gordon LLP

(57) ABSTRACT

There is provided a biological information monitoring system for monitoring biological information of a subject on a bed, the system comprising: detectors which detect load of the subject; a center of gravity position calculating unit which acquires temporal variation of a center of gravity position of the subject based on the detected load; a body motion information determining unit which acquires infor-
(Continued)

mation on body motion of the subject based on the acquired temporal variation; and a respiratory rate calculating unit which calculates a respiratory rate of the subject based on the acquired temporal variation and the information on the body motion of the subject. The body motion information includes information on large and small body motions of the subject, and the body motion information determining unit includes first and second body motion information determining units which determine the information on the large and small body motions of the subject, respectively.

21 Claims, 17 Drawing Sheets

(51) Int. Cl.
  *A61B 5/11*  (2006.01)
  *A61B 5/113*  (2006.01)
  *A61B 5/0255*  (2006.01)
  *A61B 5/0205*  (2006.01)
  *A61B 5/024*  (2006.01)

(52) U.S. Cl.
  CPC .......... *A61B 5/0816* (2013.01); *A61B 5/1102* (2013.01); *A61B 5/113* (2013.01); *A61B 5/1115* (2013.01); *A61B 5/1121* (2013.01); *A61B 5/4809* (2013.01); *A61B 5/4818* (2013.01); *A61B 5/6891* (2013.01); *A61B 5/7207* (2013.01); *A61B 5/7282* (2013.01); *A61B 5/024* (2013.01); *A61B 2562/0252* (2013.01); *A61B 2562/046* (2013.01)

(58) Field of Classification Search
  CPC ... A61B 5/4818; A61B 5/6891; A61B 5/7207; A61B 5/7282; A61B 5/024; A61B 5/0255; A61B 5/1102; A61B 5/1115; A61B 5/1121; A61B 2562/0252; A61B 2562/046
  See application file for complete search history.

(56) References Cited

U.S. PATENT DOCUMENTS

| | | | |
|---|---|---|---|
| 2007/0149883 A1* | 6/2007 | Yesha | A61B 5/1102 600/485 |
| 2007/0191742 A1 | 8/2007 | Park | |
| 2008/0275349 A1 | 11/2008 | Halperin et al. | |
| 2008/0306379 A1 | 12/2008 | Ikuma et al. | |
| 2009/0137933 A1* | 5/2009 | Lieberman | A61B 5/1036 600/595 |
| 2009/0149779 A1* | 6/2009 | Russo | A61B 5/02405 600/595 |
| 2011/0046498 A1 | 2/2011 | Klap et al. | |
| 2011/0112442 A1 | 5/2011 | Meger et al. | |
| 2012/0116187 A1 | 5/2012 | Hayes et al. | |
| 2012/0132211 A1 | 5/2012 | Halperin et al. | |
| 2012/0179040 A1 | 7/2012 | Arai et al. | |
| 2012/0184851 A1 | 7/2012 | Arai et al. | |
| 2012/0184852 A1 | 7/2012 | Arai et al. | |
| 2012/0253142 A1 | 10/2012 | Meger et al. | |
| 2013/0267791 A1* | 10/2013 | Halperin | A61B 5/002 600/300 |
| 2014/0005502 A1 | 1/2014 | Klap et al. | |
| 2014/0046209 A1 | 2/2014 | Klap et al. | |
| 2014/0350351 A1 | 11/2014 | Halperin et al. | |
| 2014/0371635 A1 | 12/2014 | Shinar et al. | |
| 2015/0164438 A1 | 6/2015 | Halperin et al. | |
| 2016/0093196 A1 | 3/2016 | Shinar et al. | |
| 2018/0220897 A1 | 8/2018 | Meger et al. | |
| 2019/0254570 A1 | 8/2019 | Shinar et al. | |
| 2019/0320987 A1 | 10/2019 | Halperin et al. | |

FOREIGN PATENT DOCUMENTS

| | | |
|---|---|---|
| JP | 6124010 B2 | 6/1986 |
| JP | H08-80285 A | 3/1996 |
| JP | 2000316915 A | 11/2000 |
| JP | 2004202043 A | 7/2004 |
| JP | 4002905 B2 | 11/2007 |
| JP | 2008301970 A | 12/2008 |
| JP | 2010148700 A | 7/2010 |
| JP | 2011083636 A | 4/2011 |
| JP | 4829020 B2 | 11/2011 |
| JP | 2012011174 A | 1/2012 |
| JP | 4883380 B2 | 2/2012 |
| JP | 2014180432 A | 9/2014 |
| WO | 2011009085 A2 | 1/2011 |
| WO | 2015011591 A1 | 1/2015 |
| WO | 2015086414 A1 | 6/2015 |

OTHER PUBLICATIONS

International Search Report for corresponding International Application No. PCT/JP2016/004342 dated Dec. 5, 2016.
"A Time-Frequency Respiration Tracking System using Non-Contact Bed Sensors with Artifact Rejection" by Zachary T. Beattie, et al., IEEE Eng Med Biol Soc., Aug. 2015; pp. 8111-8114.
Japanese Office Action for corresponding Application No. JP2015-210444 dated Jul. 26, 2016.
Japanese Office Action for corresponding Application No. JP2015-210444 dated Oct. 11, 2016.
Japanese Decision to Grant a Patent for corresponding Application No. 2015-210444 dated Jan. 23, 2017.
Written Opinion of the International Searching Authority for International Application No. PCT/JP2016/004342 dated Dec. 5, 2016.
European Office Action for corresponding European Application No. 16779192.0 dated Nov. 28, 2018.
Notice of Reasons for Rejection for Japanese Patent Application No. 2017-236140 dated Dec. 4, 2018 and partial English translation.
Zachary T Beattie et al; "Classification of lying position using load cells under the bed", Engineering in Medicine and Biology Society, EMBC, 2011 annual International Conference of the IEEE, IEEE, Aug. 30, 2011 (Aug. 30, 2011), pp. 474-477, XP032318668, DOI: 10.1109/IEMBS.2011.6090068 ISBN: 978-1-4244-4121-1.
Chinese Office Action dated Dec. 26, 2019 for corresponding Chinese Application No. 201680047764.3 and English Translation.
Zachary T. Beattie et al., "Classification of Lying Position Using Load Cells under the Bed", 2011 Annual International Conference of the IEEE Engineering in Medicine and Biology, Boston, MA, USA, Sep. 3, 2011, pp. 474-477.
Adriana M. Adami et al., "A Gaussian Model for Movement Detection during Sleep", 2012 Annual International Conference of the IEEE Engineering in Medicine and Biology, Sep. 1, 2012, pp. 2263-2266.

\* cited by examiner

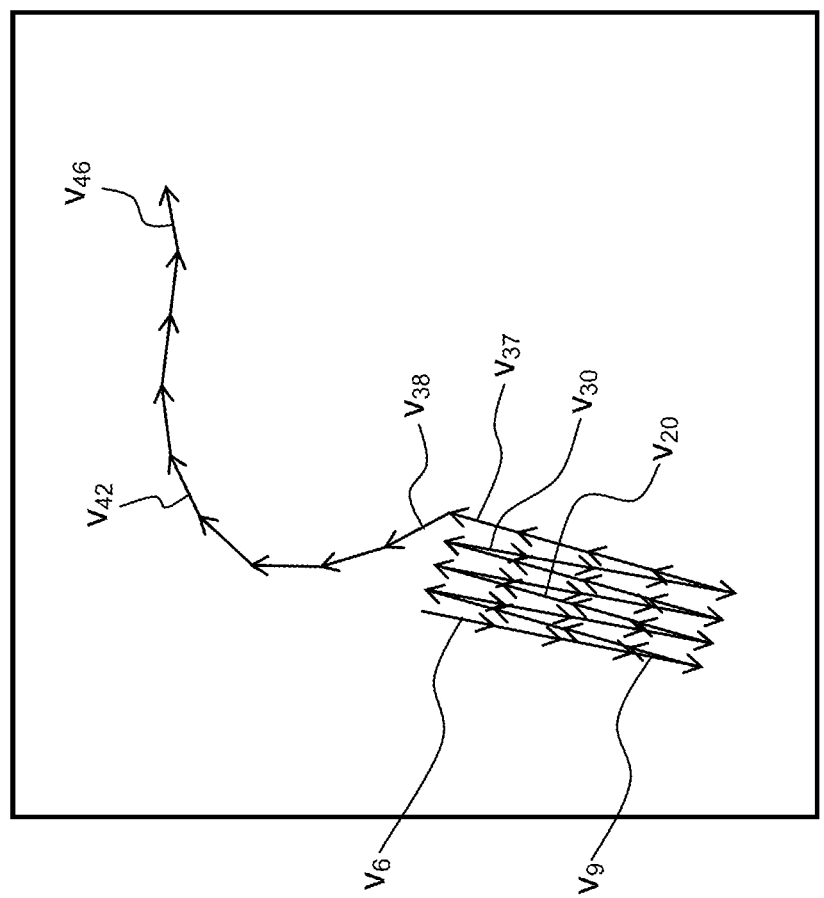

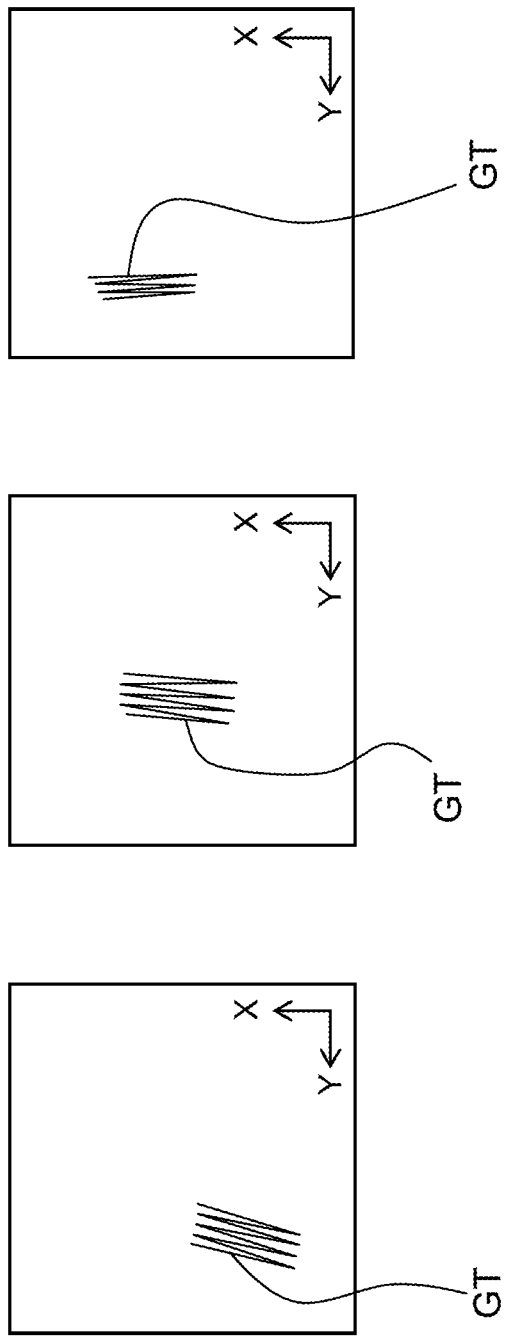

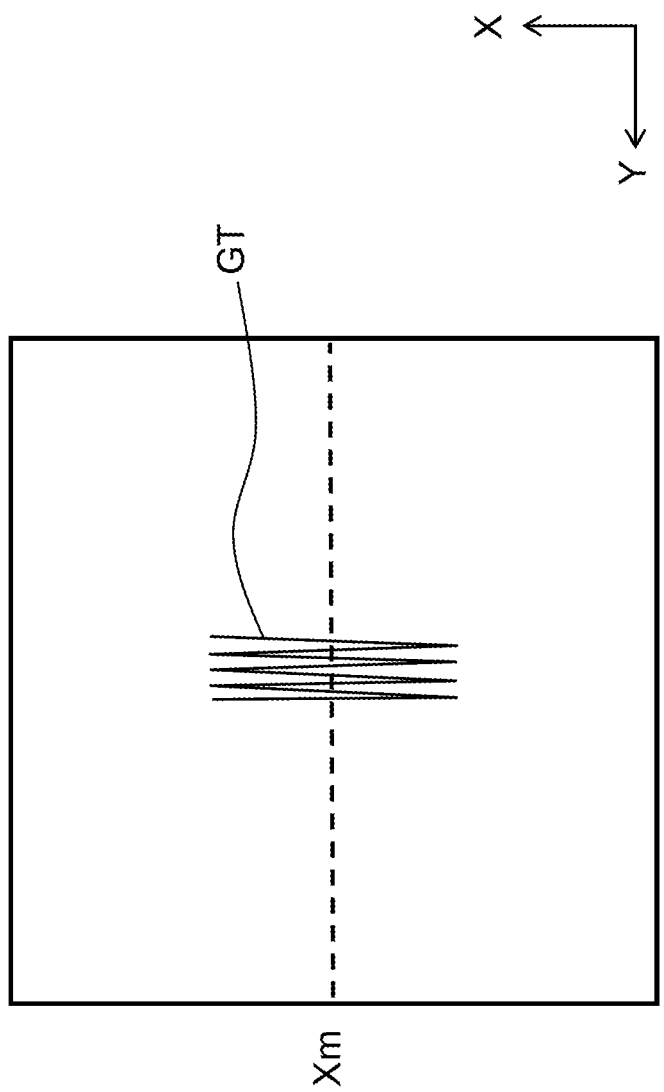

BIOMETRIC INFORMATION MONITORING SYSTEM

CROSS-REFERENCE TO RELATED APPLICATIONS

This application is a Continuation Application of International Application No. PCT/JP2016/004342 claiming the conventional priority of Japanese patent Application No. 2015-191959 filed on Sep. 29, 2015 and Japanese patent Application No. 2015-210444 filed on Oct. 27, 2015, and titled "BIOMETRIC INFORMATION MONITORING SYSTEM". The disclosures of Japanese patent Applications No. 2015-191959 and No. 2015-210444, and International Application No. PCT/JP2016/004342 are incorporated herein by reference in their entirety.

BACKGROUND

The present disclosure relates to a monitoring system for monitoring biometric information (biological information) by using a bed sensor.

Biometric information of a subject (human subject, that is, a person being monitored) is one of important pieces of information for knowing the physical condition (body condition) of a patient or a care receiver in the sites of the medical treatment and the care. For example, the respiratory rate of the subject can be utilized to grasp the symptoms of, for example, the sleep apnea syndrome (SAS) and the snore; and to improve (alleviate) the symptoms. Further, it is also useful to grasp how body of the patient or the care receiver is moved on a bed.

The biometric information, for example, the respiratory rate, which is obtained during the sleep of a subject, is generally measured by attaching a respiration sensor to the nostril and attaching an acceleration sensor to the breast and/or the abdomen. Further, it has been also suggested that load sensors are arranged under feet of a bed to measure the respiratory rate of a subject on the basis of measured values of the load sensors (Japanese Patent No. 4883380). Further, it has been also suggested that load detectors are arranged under feet of a bed to acquire the movement of the center of gravity of a subject living body on the bed so that the respiratory movement (breathing movement) and the heart rate movement (heart beat movement) of the subject living body are acquired on the basis of the movement of the center of gravity (Japanese Patent Publication No. 61-24010).

SUMMARY

In the case of the method in which the sensors are attached to the nostril, the breast and/or the abdomen, it is necessary for the subject to attach the measuring devices to the body. The presence of the measuring device gives discomfort and/or unpleasantness to the subject, and may cause disturbance of sleep of the subject, restriction on actions of the subject, such as walking to a lavatory at night, and the delirium during hospitalization. Further, the measuring device may be detached from the body of the subject during the sleep of the subject depending on the postures of the subject in sleep, and may result in a failure in the measurement.

On the other hand, in the case of the methods described in Japanese Patent No. 4883380 and Japanese Patent Publication No. 61-24010 in which the load sensors are arranged under the feet of the bed, it is feared that the measurement accuracy may be insufficient. Further, in the case of the methods described in Japanese Patent No. 4883380 and Japanese Patent Publication No. 61-24010, it is impossible to highly accurately acquire both of the body motion information (information on a body motion) and the respiration information (information on respiration) of the subject.

In view of the above, an object of the present disclosure is to solve the foregoing problems and provide a monitoring system, which is a noninvasive sensor, for monitoring biometric information of a subject at a high accuracy without giving any discomfort and any unpleasantness to the subject.

According to a first aspect of the present disclosure, there is provided a biological information monitoring system for monitoring biological information of a subject on a bed, the system including: a plurality of load detectors which are placed in the bed or under feet of the bed and which detect a load of the subject; a center of gravity position calculating unit which acquires a temporal variation of a center of gravity position of the subject based on the detected load of the subject; a body motion information determining unit which acquires information on a body motion of the subject based on the acquired temporal variation of the center of gravity position of the subject; and a respiratory rate calculating unit which calculates a respiratory rate of the subject based on the acquired temporal variation of the center of gravity position of the subject and the information on the body motion of subject acquired by the body motion information determining unit, wherein the body motion information is an information on a movement of a whole body or a part of the whole body of the subject, the movement being different from a movement caused by a respiration of the subject;

the body motion information includes an information on a large body motion of the subject and an information on a small body motion of the subject, an amount of movement of the center of gravity position of the subject within a predetermined time period caused by the small body motion being smaller than an amount of movement of the center of gravity position of the subject within the predetermined time period caused by the large body motion;

the body motion information determining unit includes a first body motion information determining unit which determines the information on the large body motion of the subject and a second body motion information determining unit which determines the information on the small body motion of the subject;

the first body motion information determining unit determines a variation caused by the large body motion of the subject included in the temporal variation of the center of gravity position of the subject, based on a movement distance of the center of gravity position within a predetermined time period; and the second body motion information determining unit determines a variation, caused by the small body motion of the subject, included in the temporal variation of the center of gravity position of the subject, based on a movement direction of the center of gravity position, the temporal variation of the center of gravity position being a variation from which the variation caused by the large body motion determined by the first body motion information determining unit has been removed.

According to a second aspect of the present disclosure, there is provided a biological information monitoring system for monitoring biological information of a subject on a bed, the system including:

a plurality of load detectors which are placed in the bed or under feet of the bed and which detect a load of the subject;

a center of gravity position calculating unit which acquires a temporal variation of a center of gravity position of the subject based on the detected load of subject;

a body motion information determining unit which acquires information on a body motion of the subject based on the acquired temporal variation of the center of gravity position of the subject; and a respiratory rate calculating unit which calculates a respiratory rate of the subject based on the acquired temporal variation of center of gravity position of the subject and the information on the body motion of the subject acquired by the body motion information determining unit, wherein the body motion information is an information on a movement of a whole body or a part of the whole body of the subject, the movement being different from a movement caused by a respiration of the subject;

the temporal variation of the center of gravity position includes a variation caused by a body motion of the subject and a variation caused by a respiration of the subject; and the biological information monitoring system further comprises a body axis determining unit which acquires a body axis of the subject based on the variation caused by the respiration.

According to a third aspect of the present disclosure, there is provided a bed system includes a bed; and the biological information monitoring system according to the first or second aspect.

BRIEF DESCRIPTION OF DRAWINGS

FIG. 10 depicts a plurality of movement vectors included in the locus of the center of gravity depicted in FIG. 9A.

FIG. 11A depicts locus obtained by removing the locus of the movement of the center of gravity caused by the small body motion of the subject from the locus of the center of gravity of the subject on the bed depicted in FIG. 9A.

FIG. 11B depicts locus obtained by removing the locus of the movement of the center of gravity caused by the small body motion of the subject from the locus of the center of gravity of the subject on the bed depicted in FIG. 9B.

FIG. 11C depicts locus obtained by removing the locus of the movement of the center of gravity caused by the small body motion of the subject from the locus of the center of gravity of the subject on the bed depicted in FIG. 9C.

FIG. 12 depicts a locus obtained by rotating the locus GT of the center of gravity depicted in FIG. 11A so that the body axis direction is coincident with the X direction.

EMBODIMENTS

First Embodiment

A first embodiment of the present disclosure will be explained with reference to FIGS. 1 to 12.

Figure 1:
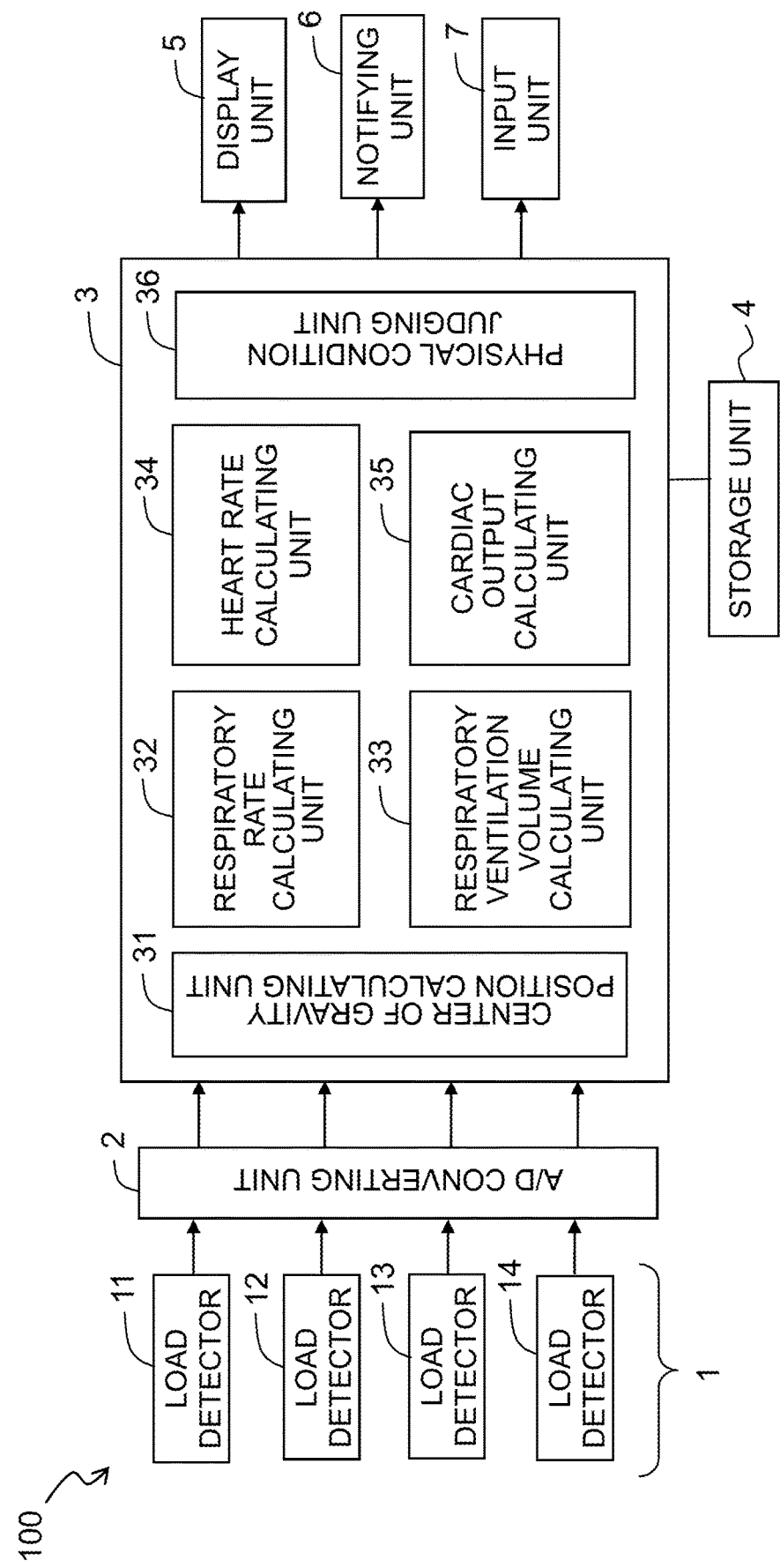
FIG. 1 is a block diagram depicting a configuration of a biometric information monitoring system according to an embodiment of the present disclosure.

As depicted in FIG. 1, a biometric information monitoring system (biological information monitoring system) 100 of this embodiment is provided to perform the observation and the measurement in order to grasp the biometric (biological) state or condition of a subject (a human subject, that is, a person being monitored) on a bed. The biometric information monitoring system 100 principally includes a load detecting unit 1, a control unit 3, a storage unit 4, and a display unit 5. The load detecting unit 1 and the control unit 3 are connected via an A/D converting unit 2. A notifying unit 6 and an input unit 7 are further connected to the control unit 3.

The load detecting unit 1 is provided with four load detectors 11, 12, 13, 14. Each of the load detectors 11, 12, 13, 14 is a load detector which detects the load by using, for example, a beam-type load cell. Such a load detector is described, for example, in Japanese Patent No. 4829020 and Japanese Patent No. 4002905. Each of the load detectors 11, 12, 13, 14 is connected to the A/D converting unit 2 by means of wiring.

The A/D converting unit 2 is provided with an A/D converter which converts the analog signal fed from the load detecting unit 1 into the digital signal. The A/D converting unit 2 is connected to each of the load detecting unit 1 and the control unit 3 by means of wiring.

The control unit 3 is an exclusive or general-purpose computer. A center of gravity position calculating unit 31, a respiratory rate calculating unit 32, a respiratory ventilation volume (tidal volume) calculating unit 33, a heart rate calculating unit 34, a cardiac output calculating unit 35, and a physical condition judging unit 36 are constructed therein.

The storage unit 4 is a storage device which stores the data used for the biometric information monitoring system 100. For example, it is possible to use a hard disk (magnetic disk) therefore. The display unit 5 is a monitor such as a liquid crystal monitor or the like for displaying the information outputted from the control unit 3 for a user of the biometric information monitoring system 100.

The notifying unit 6 is provided with a device for visually or auditorily performing predetermined notification on the basis of the information fed from the control unit 3, for example, a speaker. The input unit 7 is an interface for performing predetermined input for the control unit 3, which may be a keyboard and a mouse.

An explanation will be made about the operation for detecting and monitoring the biometric information, such as the respiratory condition of the subject on the bed, by using the biometric information monitoring system 100 described above.

Figure 2:
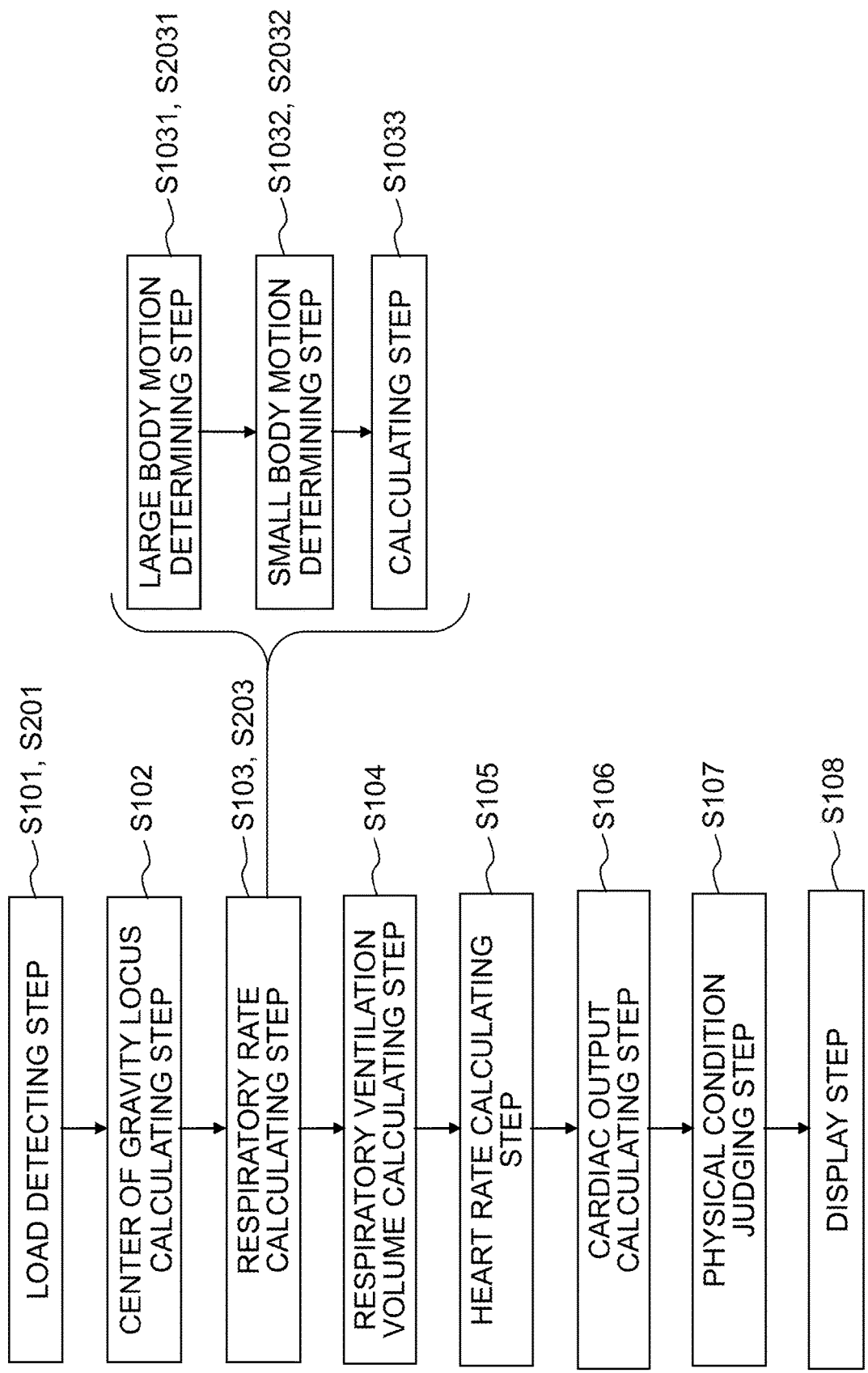
FIG. 2 is a flow chart depicting a respiratory condition detecting method according to the embodiment of the present disclosure.

As depicted in FIG. 2, the detection of the respiratory condition of the subject, which is based on the use of the biometric information monitoring system 100, includes a load detecting step (S101), a center of gravity locus calculating step (S102), a respiratory rate calculating step (S103), a respiratory ventilation volume calculating step (S104), a heart rate calculating step (S105), a cardiac output calculating step (S106), and a physical condition judging step (S107). The load detecting step (S101) is a step of detecting the load of the subject. The center of gravity locus calculating step (S102) is a step of calculating the temporal variation of the position of the center of gravity of the subject (center of gravity locus) on the basis of the detected load. The respiratory rate calculating step (S103) is a step of calculating the body motion, the respiratory condition, the respiratory rate, and the temporal change thereof of the subject on the basis of the acquired center of gravity locus. The respiratory ventilation volume calculating step (S104) is a step of calculating the ventilation volume (tidal volume) of the respiration of the subject on the basis of the acquired center of gravity locus. The heart rate calculating step (S105) is a step of calculating the heart rate of the subject on the basis of the detected load. The cardiac output calculating step (S106) is a step of calculating the cardiac output of the subject. The physical condition judging step (S107) is a step of judging the physical condition of the subject on the basis of the calculated respiratory rate and the respiratory ventilation volume of the subject. The detection of the respiratory condition of the subject further includes a display step (S108) of displaying the respiratory rate and the respiratory ventilation volume of the subject calculated in the foregoing steps and the physical condition of the subject judged in the foregoing step.

Load Detecting Step

Figure 3:
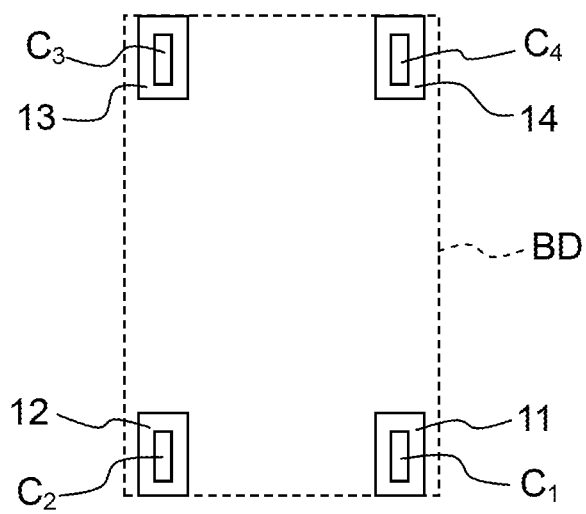
FIG. 3 is an illustrative view depicting an arrangement of load detectors with respect to a bed.

In order to perform the load detecting step S101, the four load detectors 11, 12, 13, 14 of the load detecting unit 1 are arranged under feet of a bed to be used by the subject. Specifically, as depicted in FIG. 3, the load detectors 11, 12, 13, 14 are arranged respectively under casters $C_1$, $C_2$, $C_3$, $C_4$ attached to lower end portions of the feet disposed at the four corners of the bed BD.

Figure 4:
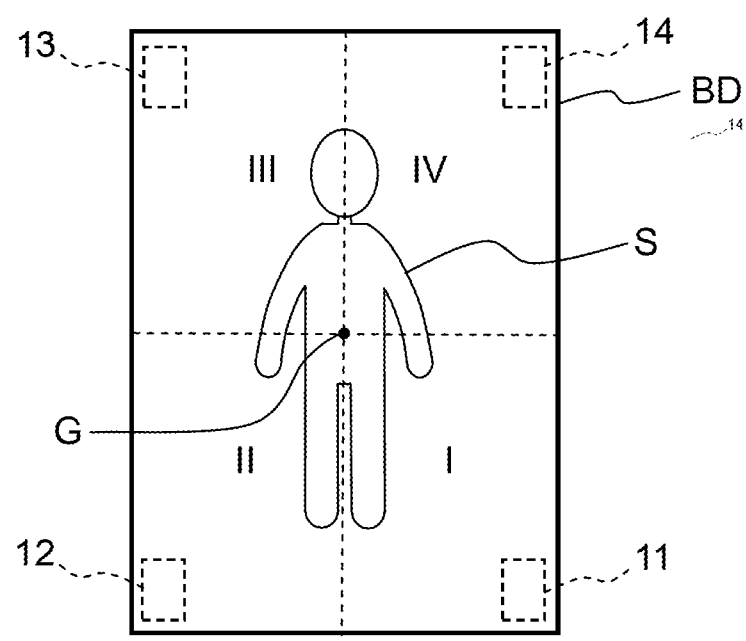
FIG. 4 is an illustrative view depicting an arrangement of four load detection areas defined on the upper surface of the bed.

When the load detectors 11, 12, 13, 14 are arranged under the casters $C_1$, $C_2$, $C_3$, $C_4$ respectively, the load, which is applied to the upper surface of the bed BD, is thereby detected in a dispersed manner by the four load detectors 11, 12, 13, 14. Specifically, as depicted in FIG. 4, the rectangular upper surface of the bed BD is longitudinally divided into two and laterally divided into two, and thus the upper surface is equally divided into four rectangular areas I to IV.

Accordingly, the load, which is applied to the area I positioned with the left lower half of the body of the subject S lying on his/her back (face up) at the central portion of the bed BD, is principally detected by the load detector 11, and the load, which is applied to the area II positioned with the right lower half of the body of the subject S in the same state, is principally detected by the load detector 12. Similarly, the load, which is applied to the area III positioned with the right upper half of the body of the subject S lying on his/her back at the central portion of the bed BD, is principally detected by the load detector 13, and the load, which is applied to the area IV positioned with the left upper half of the body of the subject S in the same state, is principally detected by the load detector 14. Note that when the subject S does not exist on the bed BD, the total of the outputs from the load detectors 11, 12, 13, 14 represents the weight of the bed itself. When the subject S exists on the bed BD, the total of the outputs from the load detectors 11, 12, 13, 14 represents the weight of the bed and the body weight of the subject S. Therefore, it is possible to measure the body weight of the subject S when the subject S exists on the bed, by previously storing the weight of the bed itself in the storage unit 4. Note that when the weight of the bed is not uniform among the four areas, the difference therebetween is stored beforehand as the bed weight corresponding to each of the load detectors. Further, it is desirable that the situation in which any weight other than that of the subject S is brought about during the actual measurement, for example, the placement of any bedding, any baggage or the like is reflected to the weight of the bed.

Each of the load detectors 11, 12, 13, 14 detects the load (load change), and the load (load change) is outputted as the analog signal to the A/D converting unit 2. The A/D converting unit 2 converts the analog signal into the digital signal while using the sampling period of, for example, 0.1 second, and the digital signal (hereinafter referred to as "load signal") is outputted to the control unit 3.

Figure 5:
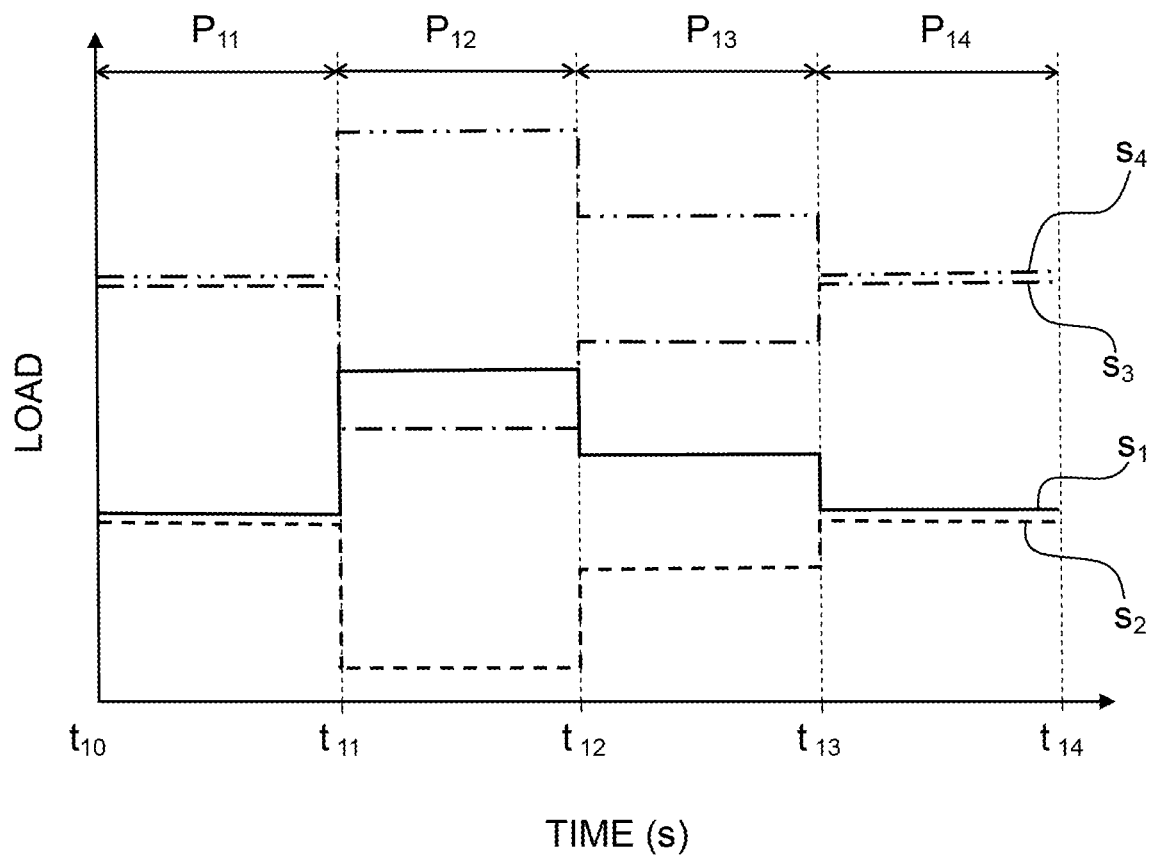
FIG. 5 depicts exemplary load signals fed from the load detectors.

Exemplary load signals are depicted in FIG. 5. FIG. 5 depicts the load signals $s_1$ (solid line), $s_2$ (broken line), $s_3$ (alternate long and short dash line), and $s_4$ (alternate long and two short dashes line) fed from the load detectors 11, 12, 13, 14 as outputted during the period ranging from the time $t_{10}$ to the time $t_{14}$. The following fact has been observed. That is, the subject S lay on his/her back at the central portion of the bed BD during the period ranging from the time $t_{10}$ to the time $t_{11}$ (period $P_{11}$) as depicted in FIG. 4. The subject S moved to the side of the areas I, IV of the bed BD during the period ranging from the time $t_{11}$ to the time $t_{12}$ (period $P_{12}$). The subject S moved to some extent to the central side of the bed BD during the period ranging from the time $t_{12}$ to the time $t_{13}$ (period $P_{13}$) as compared with the period $P_{12}$. The subject S lay on his/her back at the central portion of the bed BD during the period ranging from the time $t_{13}$ to the time $t_{14}$ (period $P_{14}$).

The subject S lay on his/her back at the central portion of the bed BD as depicted in FIG. 4 during the period $P_{11}$. Therefore, the signals $s_3$, $s_4$, which are fed from the load detectors 13, 14 arranged on the head side of the subject S, are approximately equal to one another during the period $P_{11}$, and the signals $s_1$, $s_2$, which are fed from the load detectors 11, 12 arranged on the foot side of the subject S, are approximately equal to one another.

The subject S moved to the side of the areas I, IV of the bed BD during the period $P_{12}$. Therefore, the signals $s_1$, $s_4$, which are fed from the load detectors 11, 14 arranged in the areas I, IV, exhibit the large load values during the period $P_{12}$ as compared with the period $P_{11}$, and the signals $s_2$, $s_3$, which are fed from the load detectors 12, 13 arranged in the areas II, III, exhibit the small load values as compared with the period $P_{11}$.

The subject S moved to some extent to the central side of the bed BD during the period $P_{13}$ as compared with the period $P_{12}$. Therefore, the signals $s_1$, $s_4$, which are fed from the load detectors 11, 14 arranged in the areas I, IV, exhibit the small load values during the period $P_{13}$ as compared with the period $P_{12}$, and the signals $s_2$, $s_3$, which are fed from the load detectors 12, 13 arranged in the areas II, III, exhibit the large load values as compared with the period $P_{12}$.

The subject S lay on his/her back at the central portion of the bed BD during the period $P_{14}$ in the same manner as the period $P_{11}$. Therefore, the signals $s_1$ to $s_4$, which are provided during the period $P_{14}$, are the same as the signals $s_1$ to $s_4$ provided during the period $P_{11}$. It is possible to monitor whether or not the subject exists on the bed by using the output from the load detector 1. Further, it is possible to correctly monitor the subject by using the data fed from the center of gravity position calculating unit 31 and the respiratory rate calculating unit 32 as described later on.

Center of Gravity Locus Calculating Step

Figure 6:
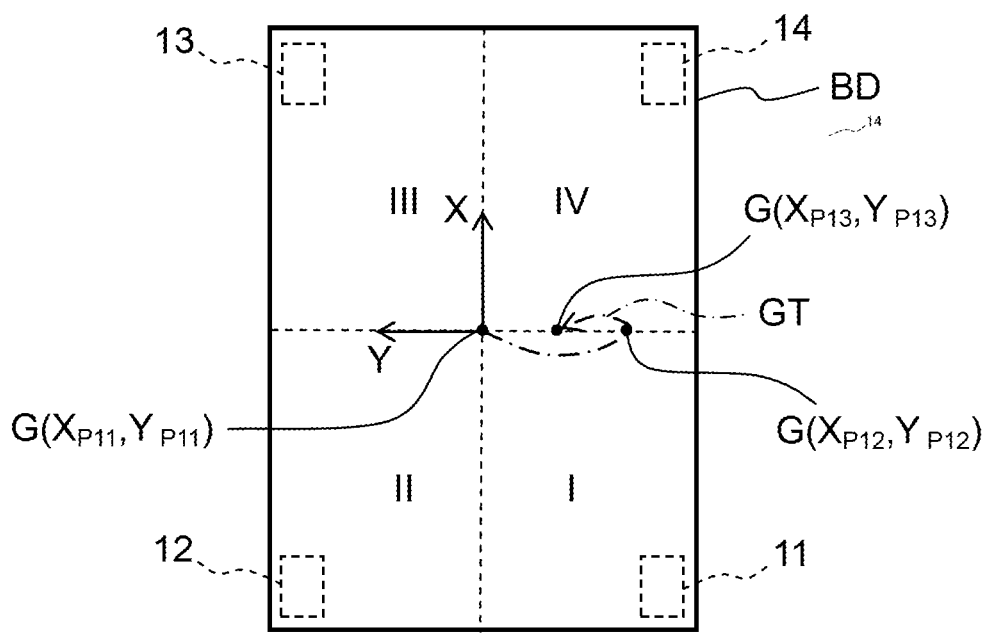
FIG. 6 depicts exemplary locus (trajectory, path) of the center of gravity of a subject.

In the center of gravity locus calculating step S102, the center of gravity position calculating unit 31 calculates the position G (X, Y) of the center of gravity G of the subject S on the bed BD at a predetermined period T (for example, a period equal to the sampling period of 0.1 second described above) on the basis of the load signals $s_1$ to $s_4$ fed from the load detectors 11 to 14 to acquire the temporal variation of the position of the center of gravity G of the subject S (center of gravity locus GT). In this case, (X, Y) indicates the coordinates on the XY coordinate plane in which X extends in the longitudinal direction of the bed BD and Y extends in the lateral direction of the bed BD while the central portion of the bed BD is the origin (FIG. 6).

The calculation of the position G (X, Y) of the center of gravity G by the center of gravity position calculating unit 31 is performed in accordance with the following operation. That is, G (X, Y) is calculated in accordance with the following expressions assuming that the coordinates of the load detectors 11, 12, 13, 14 are $(X_{11}, Y_{11})$, $(X_{12}, Y_{12})$, $(X_{13}, Y_{13})$, and $(X_{14}, Y_{14})$ respectively, and the detection values of the load detectors 11, 12, 13, 14 are $W_{11}$, $W_{12}$, $W_{13}$, and $W_{14}$ respectively.

$$X = \frac{X_{11} \times W_{11} + X_{12} \times W_{12} + X_{13} \times W_{13} + X_{14} \times W_{14}}{W_{11} + W_{12} + W_{13} + W_{14}} \quad \text{[Math. 1]}$$

$$Y = \frac{Y_{11} \times W_{11} + Y_{12} \times W_{12} + Y_{13} \times W_{13} + Y_{14} \times W_{14}}{W_{11} + W_{12} + W_{13} + W_{14}} \quad \text{[Math. 2]}$$

The center of gravity position calculating unit 31 acquires the temporal variation of the position G (X, Y of the center of gravity G, i.e., the center of gravity locus GT while calculating the position G (X, Y) of the center of gravity G at the predetermined sampling period T on the basis of the numerical expressions (1) and (2) described above. The acquired center of gravity locus GT is stored, for example, in the storage unit 4.

An example of the center of gravity locus GT calculated by the center of gravity position calculating unit 31 is depicted in FIG. 6. FIG. 6 depicts the positions G $(X_{P11}, Y_{P11})$, G $(X_{P12}, Y_{P12})$, G $(X_{P13}, Y_{P13})$ of the center of gravity G of the subject S on the bed BD at the times $t_{110}$, $t_{120}$, $t_{130}$ included in the periods $P_{11}$, $P_{12}$, $P_{13}$ depicted in FIG. 5 respectively. An arrow of alternate long and short dash line to connect $P_{11}$, $P_{12}$, $P_{13}$ indicates the center of gravity locus GT of the center of gravity G of the subject S moving from the position G $(X_{P11}, Y_{P11})$ to G $(X_{P13}, Y_{P13})$. When the center of gravity locus GT calculated by the center of gravity position calculating unit 31 is used, it is thereby possible to monitor that the subject S exists on the bed if the center of gravity locus GT varies or the subject S does not exist on the bed if the center of gravity locus GT does not vary.

Respiratory Rate Calculating Step

In the respiratory rate calculating step S103, the respiratory rate calculating unit 32 calculates the respiratory rate per unit time of the subject S on the basis of the center of gravity locus GT calculated by the center of gravity position calculating unit 31.

The respiration of human is performed by moving the chest and the diaphragm to expand and shrink the lungs. In this context, when the air is inhaled, i.e., when the lungs are expanded, the diaphragm is lowered downwardly, and the internal organs are also moved downwardly. On the other hand, when the air is expired, i.e., when the lungs are shrunk, the diaphragm is raised upwardly, and internal organs are also moved upwardly. As a result of the research performed by the inventors of the present invention, it has been found out that the center of gravity G slightly moves in accordance with the movement of the internal organs, and the movement of the center of gravity G occurs approximately along the extending direction of the backbone (body axis direction).

Therefore, the respiratory rate calculating unit 32 can calculate the respiratory rate per unit time of the subject S on the basis of the locus of the reciprocating motion in the body axis direction of the center of gravity G included in the center of gravity locus GT calculated by the center of gravity position calculating unit 31.

Specifically, the respiratory rate calculating step S103, in which the respiratory rate calculating unit 32 calculates the respiratory rate, includes a large body motion determining step S1031, a small body motion determining step S1032 and a calculating step S1033. The large body motion determining step S1031 is a step of determining the locus of the center of gravity movement caused by the large body motion such as the turning over (tossing and turning) or the like of the subject S included in the center of gravity locus GT of the subject S. The small body motion determining step S1032 is a step of determining the locus of the center of gravity movement caused by the small body motion such as the movement of hands and feet or the like of the subject S. The calculating step S1033 is a step of calculating the respiratory rate of the subject S by using the locus of the center of gravity movement caused by the respiration of the subject S extracted as a result of these steps S1031 and S1032. More detailed procedures of the respiratory rate calculating step S103 will be explained as exemplified by a case in which the respiratory rate per one minute is calculated by way of example.

Figure 7:
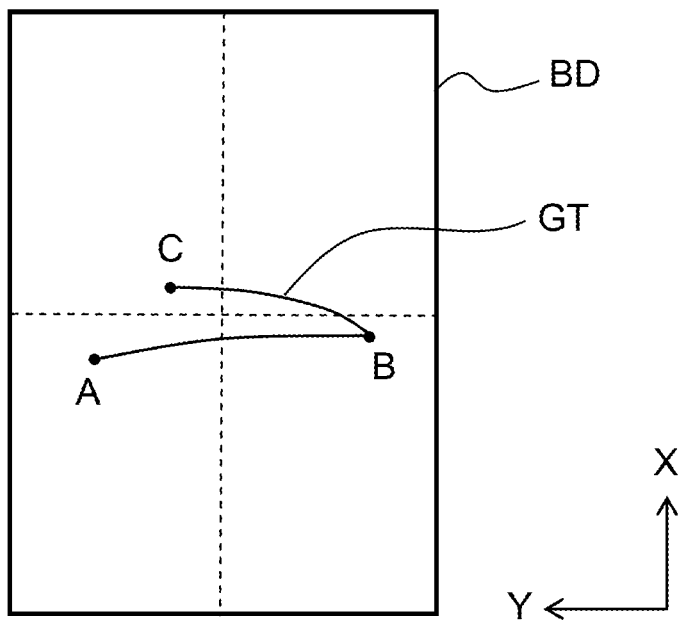
FIG. 7 depicts another exemplary locus of the center of gravity of the subject.

At first, the respiratory rate calculating unit 32 extracts, from the storage unit 4, the center of gravity locus GT of the subject S per one minute (i.e. the measurement objective period). An example of the center of gravity locus GT to be extracted is as depicted in FIG. 7. The center of gravity locus GT depicted in FIG. 7 indicates that the subject S makes one reciprocating motion in the left-right direction on the bed in accordance with, for example, the turning over during one minute as the measurement objective period. In the first movement, the center of gravity G of the subject S moves from the point A to the point B. In the second movement, the center of gravity G of the subject S moves from the point B to the point C. Note that the scale of the center of gravity movement, which is caused by the respiration of the subject S, is not expressed in FIG. 7, because it is extremely smaller than the scale of the center of gravity movement which is caused by the turning over of the subject S.

Subsequently, the respiratory rate calculating unit 32 determines, in the large body motion determining step S1031, the locus of the center of gravity movement caused by the large body motion of the subject S from the center of gravity locus GT, and the locus is removed. In the present disclosure, the term "large body motion" principally includes the turning over and other discrete body motion accompanied by the movement of the body portion, and the large body motion also arises, for example, when the subject is painful or the subject awakens. When the term is defined in view of the movement of the center of gravity, the term means the body motion in which the center of gravity G is moved beyond a predetermined distance d in a certain direction within a certain period. Therefore, it is arbitrary that what one of the body motions of the subject S is the "large body motion". It is possible to determine what one is the "large body motion" on the basis of the value of the predetermined distance d. It is also possible to define that the large body motion is the movement of the center of gravity which is larger than the movement of the center of gravity caused by the respiration to such an extent that the relative distinction can be made (for example, the former is not less than several times of the latter).

The respiratory rate calculating unit 32 judges that the large body motion occurs if the center of gravity G moves beyond the predetermined distance d substantially in one direction, and the respiratory rate calculating unit 32 removes the center of gravity locus GT corresponding to the period in which the center of gravity G moved beyond the predetermined distance d substantially in one direction. It is possible to judge whether or not the center of gravity G moves substantially in one direction, for example, on the basis of whether or not the angle, which is formed between the motion vector of the center of gravity G provided during a predetermined sampling period and the motion vector of the center of gravity G provided during the next sampling period, is not more than a predetermined angle. Note that the large body motion, which is obtained in the large body motion determining step S1031, principally includes the turning over and other body motion accompanied by the movement of the body portion. Therefore, it is possible to monitor the turning over and the movement of the posture by judging the content of the signal corresponding to the large body motion with the machine learning or the like.

Figure 8:
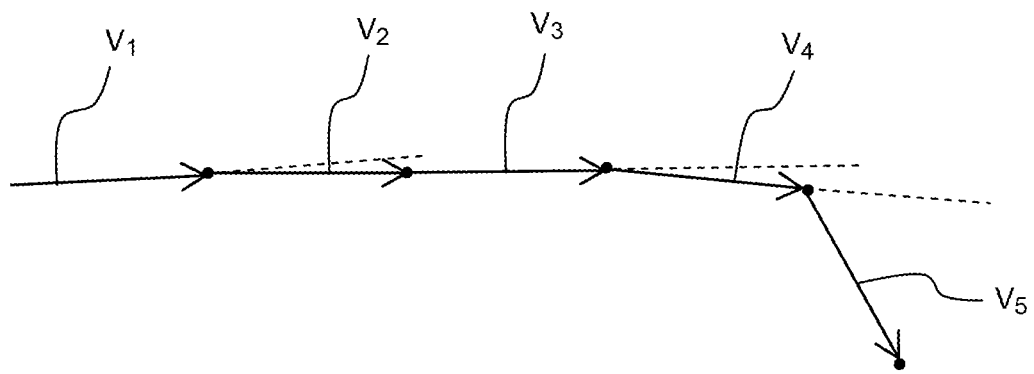
FIG. 8 is an illustrative view for explaining a method for judging the movement direction of the movement vector.

As depicted in FIG. 8, each of the motion vectors $v_2$ to $v_4$ of the center of gravity G has the angle of not more than about 5° with respect to the motion vector during the immediately preceding sampling period. However, the motion vector $v_5$ has the angle of not less than 5° with respect to the motion vector $v_4$ during the immediately preceding sampling period. In such a situation, the following assumption can be made. That is, the center of gravity G moves in a substantially constant direction during the sampling period corresponding to each of the motion vectors $v_1$ to $v_4$, and the movement direction is changed during the sampling period corresponding to the motion vector $v_5$. In this section, the threshold value (5°) of the angle is referred to by way of example, and the setting can be made to any arbitrary angle. Note that the center of gravity locus GT may be subjected to the filtering with a low-pass filter prior to determine the large body motion based on the use of the motion vector. Accordingly, the high frequency component (noise) is removed, and it is possible to improve the accuracy of determination.

Figure 9A:
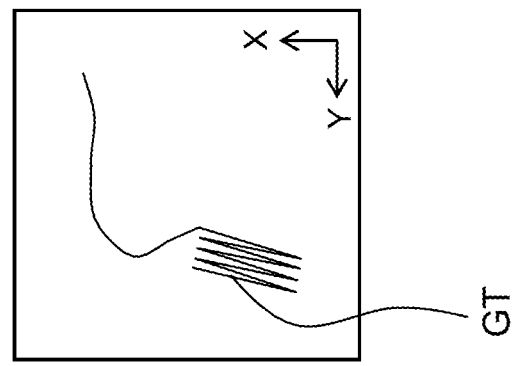
FIG. 9A depicts locus obtained by removing the locus of the movement of the center of gravity caused by the large body motion of the subject from the locus of the center of gravity of the subject on the bed depicted in FIG. 7.
Figure 9B:
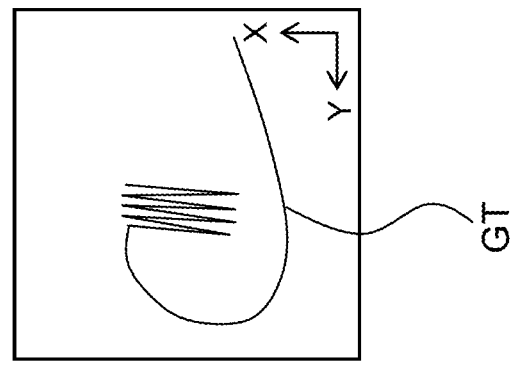
FIG. 9B depicts locus obtained by removing the locus of the movement of the center of gravity caused by the large body motion of the subject from the locus of the center of gravity of the subject on the bed depicted in FIG. 7.
Figure 9C:
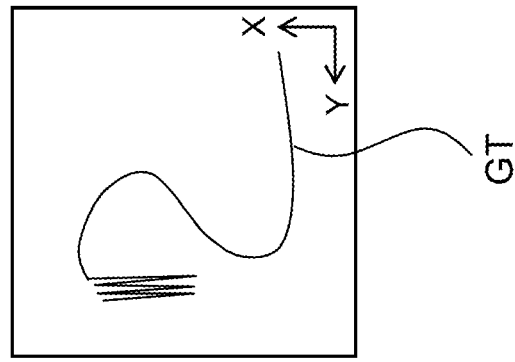
FIG. 9C depicts locus obtained by removing the locus of the movement of the center of gravity caused by the large body motion of the subject from the locus of the center of gravity of the subject on the bed depicted in FIG. 7.

When the locus of the center of gravity movement caused by the large body motion is removed from the center of gravity locus GT depicted in FIG. 7, the loci, such as depicted in FIGS. 9A to 9C, are obtained. FIG. 9A depicts the center of gravity locus GT of the subject S during the period provided before the subject S performs the first large body motion, i.e., the period in which the center of gravity G of the subject S is positioned in the vicinity of the point A depicted in FIG. 7. FIG. 9B depicts the center of gravity locus GT of the subject S during the period provided until the subject S performs the second large body motion after performing the first large body motion, i.e., the period in which the center of gravity G of the subject S is positioned in the vicinity of the point B depicted in FIG. 7. FIG. 9C depicts the center of gravity locus GT of the subject S during the period provided after the subject S performs the second large body motion, i.e., the period in which the center of gravity G of the subject S is positioned in the vicinity of the point C depicted in FIG. 7.

Each of the center of gravity loci GT depicted in FIGS. 9A to 9C includes the locus which indicates the reciprocating motion in one direction. This locus is the locus of the center of gravity movement caused by the respiration of the subject S. Each of the center of gravity loci GT depicted in FIGS. 9A to 9C further includes the part which is deviated from the reciprocating motion and which moves slightly largely in arbitrary directions. This part is the locus of the center of gravity movement caused by the small body motion of the subject S. In the present disclosure, the term "small body motion" means such a movement that the entire body of the subject S does not greatly move but only parts of the body, i.e., hands, feet, and/or face (head) move. When the small body motion is defined in view of the movement of the center of gravity, it means the body motion in which the center of gravity G is moved within a range not exceeding the predetermined distance d in the direction different from the direction of the center of gravity movement caused by the respiration of the subject S. The small body motion can be also recognized as the small movement of the center of gravity to such an extent that the small body motion can be distinguished from the large body motion (for example, the former is not more than a fraction (one-severalth) of the latter).

Subsequently, in the small body motion determining step S1032, the respiratory rate calculating unit 32 determines the locus of the center of gravity movement which is caused by the small body motion of the subject S and which is included in the center of gravity locus GT, and removes the determined locus. The locus of the center of gravity movement caused by the small body motion can be removed, for example, in accordance with the method of outlier removal.

Specifically, it is assumed that the center of gravity locus GT depicted in FIG. 9A includes forty-one motion vectors from $v_6$ to $v_{46}$ as depicted in FIG. 10. At first, the respiratory rate calculating unit 32 acquires the direction of the mode vector $v_f$ from the forty-one motion vectors. The motion vectors $v_6$ to $v_{46}$ have the directions respectively. However, as depicted in FIG. 10, some of the motion vectors $v_6$ to $v_{46}$ have mutually identical directions respectively. The direction of the mode vector $v_f$ is equal to the direction which appears most frequently and which is included in the directions of the motion vectors $v_6$ to $v_{46}$. As clarified from FIG. 10, the direction of the mode vector is equal to the direction of any one of the motion vectors $v_6$ to $v_{37}$. The direction of the mode vector $v_f$ is also approximately equal to the direction in which the body axis of the subject S extends. Therefore, it is possible to acquire the direction in which the body axis of the subject S extends, by acquiring the direction of the mode vector $v_f$. (The respiratory rate calculating unit 32 can be regarded as including a body axis determining unit.)

Subsequently, the respiratory rate calculating unit 32 regards, as the majority vector, such a motion vector included in the motion vectors $v_6$ to $v_{46}$ that the difference between the direction of the vector itself and the direction of the mode vector $v_f$ (or the direction having an angle of 180° with respect to the direction of the mode vector $v_f$) is not more than a certain threshold value, while the respiratory rate calculating unit 32 regards, as the minority vector, such a motion vector that the difference between the direction of the vector itself and the direction of the mode vector $v_f$ (and the direction having an angle of 180° with respect to the direction of the mode vector $v_f$) is larger than a certain threshold value. Specifically, the motion vectors $v_6$ to $v_{37}$, which have the direction extending substantially along the body axis direction of the subject S, are regarded as the majority vectors, and the other motion vectors $v_{38}$ to $v_{46}$ are regarded as the minority vectors. Then, the minority vectors are removed (majority vectors are extracted). By doing so, the respiratory rate calculating unit 32 removes the locus of the movement of the center of gravity G caused by the body motion of the subject S, i.e., the body motion component of the center of gravity locus GT obtained in the first half of the small body motion determining step S1032, and the respiratory rate calculating unit 32 extracts the locus of the movement of the center of gravity G caused by the respiration of the subject S, i.e., the respiratory component of the center of gravity locus GT (second half of the small body motion determining step S1032).

Further, the respiratory rate calculating unit 32 removes the locus of the movement of the center of gravity G caused by the body motion of the subject S (body motion component of the center of gravity locus GT obtained in the first half of the small body motion determining step S1032) from each of the center of gravity loci GT depicted in FIGS. 9B and 9C as well in the same manner as described above, and the respiratory rate calculating unit 32 extracts the locus of the movement of the center of gravity G caused by the respiration of the subject S (respiratory component of the center of gravity locus GT) (second half of the small body motion determining step S1032). Note that the small body motion component, which is obtained in the first half of the small body motion determining step S1032, is the movement in which only part(s) of the body, i.e., hands, feet and/or face (head) move(s). Therefore, the occurrence of, for example, the convulsion of finger, the hiccup or the like may be monitored by judging the content of the signal corresponding to the small body motion with the machine learning or the like. Further, it is also allowable to estimate whether the subject is awaken or asleep by using the small body motion.

The respiratory components, which are extracted from the center of gravity loci GT depicted in FIGS. 9A to 9C, are depicted in FIGS. 11A to 11C respectively. The total number of times of the reciprocating motion of the center of gravity locus GT depicted in FIGS. 11A to 11C represents the respiratory rate of the subject S per 1 minute. Therefore, the respiratory rate calculating unit 32 calculates the respiratory rate per 1 minute of the subject S on the basis of the center of gravity locus GT depicted in FIGS. 11A to 11C.

Specifically, the respiratory rate calculating unit 32 firstly rotates the respiratory component of the center of gravity locus GT of the subject S so that the direction of the mode vector $v_f$ is coincident with the X axis direction (FIG. 12). Subsequently, the respiratory rate calculating unit 32 performs the filtering of a plurality of stages for the center of gravity locus GT depicted in FIG. 12 by using a multi-stage filter bank. The high frequency component is removed as the noise in the filtering at each stage. On the other hand, the filtering at the next stage is performed for the low frequency component obtained by the filtering at each stage. After performing the filtering a number of times corresponding to the predetermined number of stages, the low frequency component obtained at the final stage can be regarded as the number of times of respiration. Further, it is possible to perform the correct monitoring for whether the subject exists on the bed or does not exist on the bed, by using the output from the load detecting unit 1 described above and the data of the respiratory rate calculating unit 32. For example, when any baggage or the like is placed on the bed, the output of the load detecting unit 1 changes. In this case, if the respiratory rate is calculated by the respiratory rate calculating unit 32 on the basis of the output of the load detecting unit 1, it is possible to judge that what exists on the bed is human subject not the baggage or the like. Further, when the load, based on which the respiration has been successfully detected, still exists, and the respiratory component cannot be detected anymore, then it is considered that the respiratory arrest has occurred. If the heart beat variation is not observed as well, it is meant that the cardiac arrest has occurred. In other words, it is also possible to judge at what point in time the subject died. It is also possible to speculate the situation to result in the death of the subject by means of, for example, the analysis of the body motion, the respiration, and the heart beat provided during a period preceding the death of the subject. This is extremely important, for example, for the investigation of any medical accident.

Respiratory Ventilation Volume Calculating Step

In the respiratory ventilation volume calculating step S104, the respiratory ventilation volume calculating unit 33 estimates the ventilation volume of one respiration cycle of the subject S, on the basis of the locus of the center of gravity movement based on the respiration (FIG. 12) extracted by the respiratory rate calculating unit 32. Note that the respiratory ventilation volume is the physical amount corresponding to the depth of respiration.

The amplitude of one cycle depicted in FIG. 12 corresponds to one respiration cycle. In the case of the large and deep respiration, when the lungs expand during the inhalation, then the diaphragm is greatly moved and lowered downwardly as compared with the ordinary inhalation, and the internal organs are also greatly moved downwardly. On the other hand, upon the expiration, i.e., when the lungs shrink, then the diaphragm is greatly moved and raised upwardly as compared with the ordinary expiration, and the internal organs are also greatly moved upwardly. On the contrary, in the case of the small and shallow respiration, the movement of the internal organs is small as compared with the ordinary state. According to the research performed by the inventors of the present invention, it has been found out that the slight movement of the center of gravity G caused by the movement of internal organs is affected by the size or magnitude of the respiration. Specifically, the amplitude is increased as compared with the ordinary state when the respiration is large and deep, while the amplitude is decreased as compared with the ordinary state when the respiration is small and shallow. The ventilation volume of one respiration cycle can be estimated by being correlated with the amplitude. For example, the following procedure is performed in advance. That is, the subject performs the large and deep respiration in a state in which the subject lies on his/her back on the bed, and the ventilation volume and the amplitude obtained in this state are recorded beforehand. Further, the subject performs the small and shallow respiration, and the ventilation volume and the amplitude obtained in this state are recorded beforehand. The respiratory ventilation volume is calculated using the amplitude of the acquired center of gravity locus based on the respiration. It is also possible to estimate a minute volume (a ventilation volume per one minute) by estimating the ventilation volume of one respiration cycle. When the number of times of respiration per one minute and the minute volume are known, it is thereby possible to monitor whether the respiratory condition of the subject S is comprehensively in a good state or in a bad state.

Heart Rate Calculating Step

In the heart rate calculating step S105, the heart rate calculating unit 34 extracts the heart beat component from the load signal fed from the load detecting unit 1. Specifically, the following method is used. The heart beat component is the signal component existing in a band of 0.5 Hz to 2.5 Hz. Therefore, the heart rate calculating unit 34 extracts the signal components in this frequency band from the output values of the four load detectors 11 to 14. Subsequently, the heart rate calculating unit 34 calculates the center of gravity locus based on the heart beat component in accordance with the same or equivalent method as that used in the center of gravity locus calculating step S102 to calculate the heart rate per unit time of the subject S based on the calculated center of gravity locus.

Cardiac Output Calculating Step

In the cardiac output calculating step S106, the cardiac output calculating unit 35 estimates the cardiac output of one heart beat cycle of the subject S, on the basis of the center of gravity locus based on the heart beat extracted by the heart rate calculating unit 34. The amplitude of one cycle corresponds to one heart beat cycle, in the same manner as the respiratory ventilation volume calculating step S104. Therefore, the cardiac output of one heart beat cycle can be estimated by being correlated with the amplitude. For example, the following procedure is performed in advance. That is, the subject is in a state in which the subject lies on his/her back on the bed, and the cardiac output and the amplitude obtained in this state are recorded beforehand. The cardiac output is calculated from the amplitude on the basis of the center of gravity locus based on the acquired heart beat. According to the heart rate and the cardiac output, it is possible to monitor whether the blood pressure state of the subject S is comprehensively in a good state or in a bad state. Further, it is possible to monitor whether the health status (condition of health) of the subject S is comprehensively in a good state or in a bad state by using the number of times of respiration per one minute and the minute volume described above in combination with the heart rate and the cardiac output.

Physical Condition Judging Step

In the physical condition judging step S107, the physical condition judging unit 36 judges the physical condition of the subject S by comparing the respiratory rate of the subject S determined by the respiratory rate calculating unit 32 and the respiratory ventilation volume of the subject S calculated by the respiratory ventilation volume calculating unit 33 with the reference data stored in the storage unit 4.

The physical condition judging unit 36 can compare the calculated values of the respiratory rate and the respiratory ventilation volume of the subject S with the values of the reference data stored in the storage unit 4 to monitor, for example, whether the subject S is in the sleep state or in the wakeful state. Further, the physical condition judging unit 36 can monitor whether or not the subject S snores and whether or not the subject S is in the apnea condition. Further, the physical condition judging unit 36 can monitor whether or not the subject S falls into the abnormal respiratory condition including, for example, the tachypnea, the bradypnea, the hyperpnea, and the irregular respiration. Besides, as for other examples of the physical condition capable of being judged by the physical condition judging unit 36, it is possible to monitor, for example, not only the respiratory rate but also the length of time in which the respiration stops and the length of time in which the subject performs the respiration. Further, the direction of the body axis is known. Therefore, it is also possible to monitor, for example, the direction of the turning over of the subject in accordance with the large body motion.

Display Step

In the display step S108, the respiratory rate of the subject S calculated by the respiratory rate calculating unit 32, the respiratory ventilation volume of the subject S calculated by the respiratory ventilation volume calculating unit 33, the heart rate of the subject S calculated by the heart rate calculating unit 34, the cardiac output of the subject S calculated by the cardiac output calculating unit 35, and the physical condition of the subject S judged by the physical condition judging unit 36 are displayed on the monitor. The user can monitor the respiratory rate, the respiratory ventilation volume, the heart rate, the cardiac output, and the physical condition of the subject S by viewing or visually observing the monitor.

The user of the biometric information monitoring system 100 can also make the setting such that the notification is made by the notifying unit 6 if the subject S results in a predetermined condition. For example, the user can make the setting such that the notification is made if the subject S is in the apnea condition, by using the input unit 7.

The effects of the biometric information monitoring system 100 of this embodiment are summarized as follows.

The biometric information monitoring system 100 of this embodiment calculates the respiratory rate of the subject S by using the load detectors 11 to 14 arranged under the feet of the bed BD. Therefore, it is unnecessary to attach any measuring device to the body of the subject S. Neither discomfort nor sense of incongruity is Given to the subject S.

The biometric information monitoring system 100 of this embodiment calculates the respiration rate of the subject S on the basis of the locus of the position of the center of gravity G of the subject S (temporal change of the position of the center of gravity G). The information relevant to the respiration of the subject S, which is included in the locus of the position of the center of gravity G of the subject S, is stable because the output intensity thereof is constant without being affected by the position of the subject S on the bed, unlike the information relevant to the respiration of the subject S included in the output value fed from each of the load sensors 11 to 14. Therefore, the biometric information monitoring system 100 of this embodiment can correctly calculate the respiratory rate of the subject S without being affected by the position of the subject S on the bed.

The biometric information monitoring system 100 of this embodiment calculates the respiratory rate of the subject S by removing the locus of the movement of the center of gravity G caused by the body motion of the subject S from the center of gravity locus GT of the subject S and extracting only the locus of the movement of the center of gravity G caused by the respiration of the subject S. Therefore, the accuracy of the calculated respiratory rate is high. Further, it is also possible to determine the ventilation volume of the respiration of the subject S.

In particular, in the biometric information monitoring system 100 of this embodiment, the locus of the movement of the center of gravity G caused by the large body motion is removed on the basis of the movement amount of the center of gravity G from the center of gravity locus GT of the subject S, and then the locus of the movement of the center of gravity G caused by the small body motion is removed on the basis of the movement direction of the center of gravity G. The small body motion includes those in which the center of gravity position varies at a period or a magnitude approximately equivalent to that of the respiration. Therefore, it is not easy to separate them by merely using a frequency filter. However, in the embodiment described above, the locus of the movement of the center of gravity G caused by the small body motion is removed on the basis of the movement direction of the center of gravity G. Therefore, only the locus of the movement of the center of gravity G caused by the respiration of the subject S can be extracted at a low noise from the center of gravity locus GT, and it is possible to highly accurately calculate the respiratory rate of the subject S.

Modified Embodiment

Figure 13:
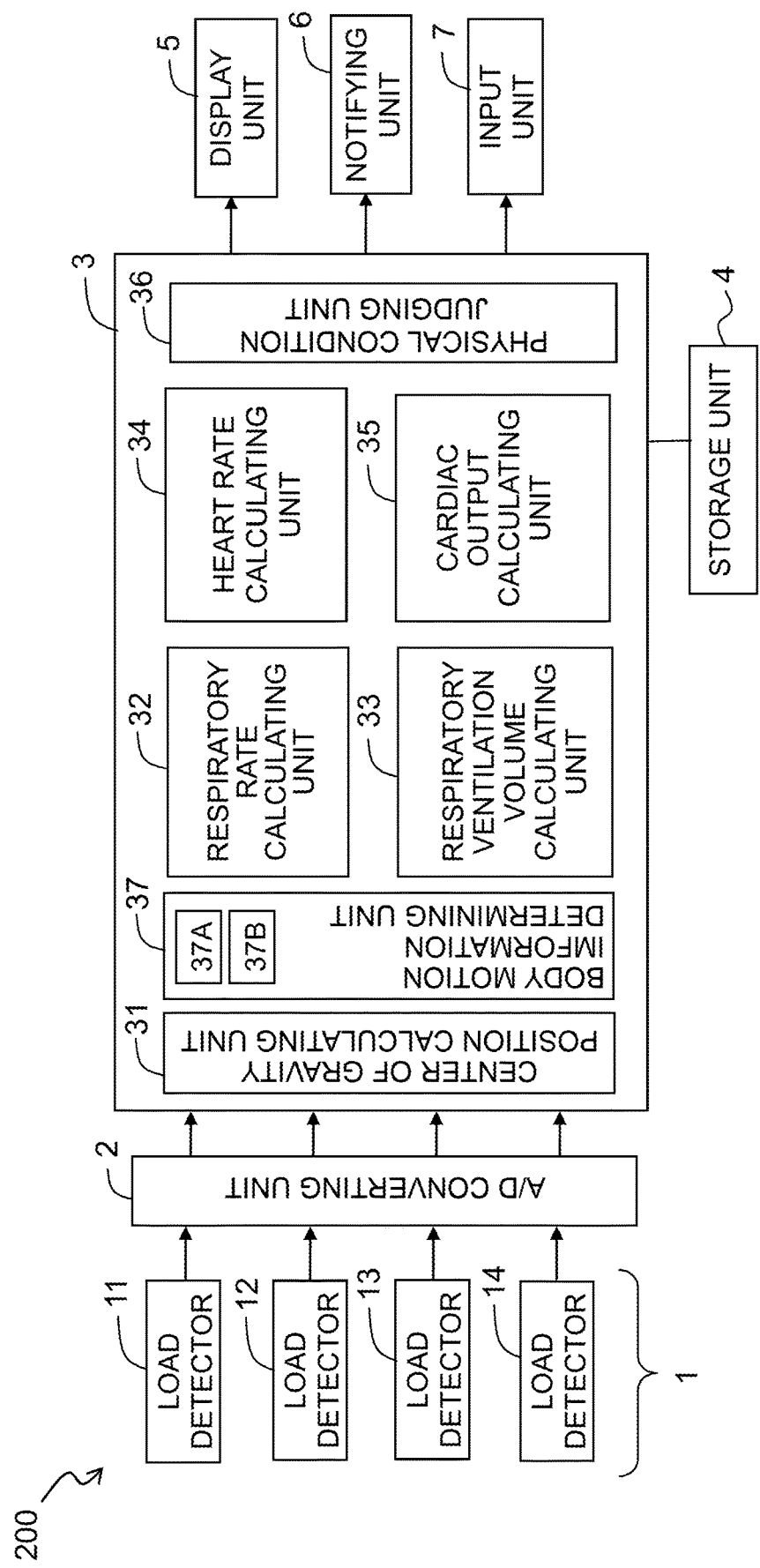
FIG. 13 is a block diagram depicting a configuration of a biometric information monitoring system according to a modified embodiment.

An explanation will be made with reference to FIGS. 13 to 19 about a modified embodiment of the method for detecting, for example, the respiratory condition of a subject by using a biometric information monitoring system 200 according to the modified embodiment (FIG. 13). The biometric information monitoring system 200 of the modified embodiment is the same as the biometric information monitoring system 100 of the embodiment described above except that the control unit 3 further comprises a body motion information determining unit 37. The method of the modified embodiment is different from the method of the embodiment described above in the process contents of the load detecting step S201 (FIG. 2) and the respiratory rate calculating step S203 (FIG. 2).

Load Detecting Step

In the load detecting step S201 of the modified embodiment, the settling of the subject S on the bed BD and the leaving of the subject S from the bed BD are also detected. Further, the body weight of the subject S is also measured.

Figure 14A:
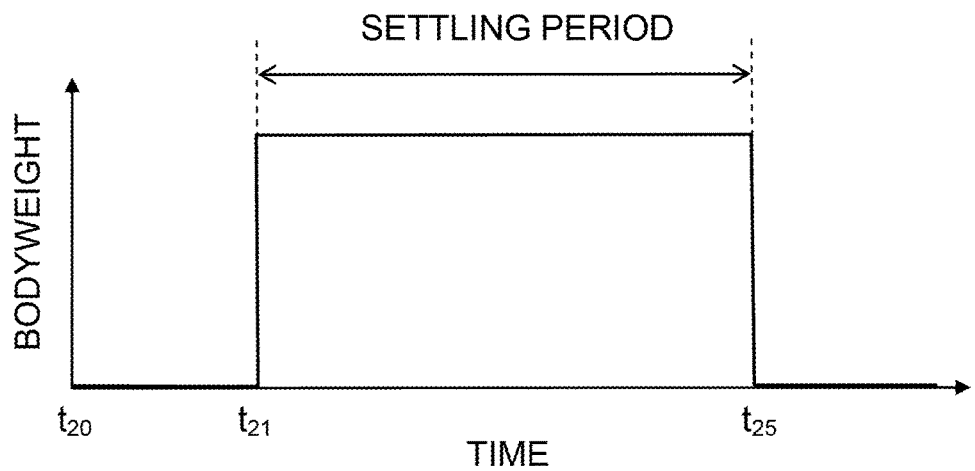
FIG. 14A depicts exemplary measured values of a body weight measured in the load detecting step according to the modified embodiment.
Figure 14B:
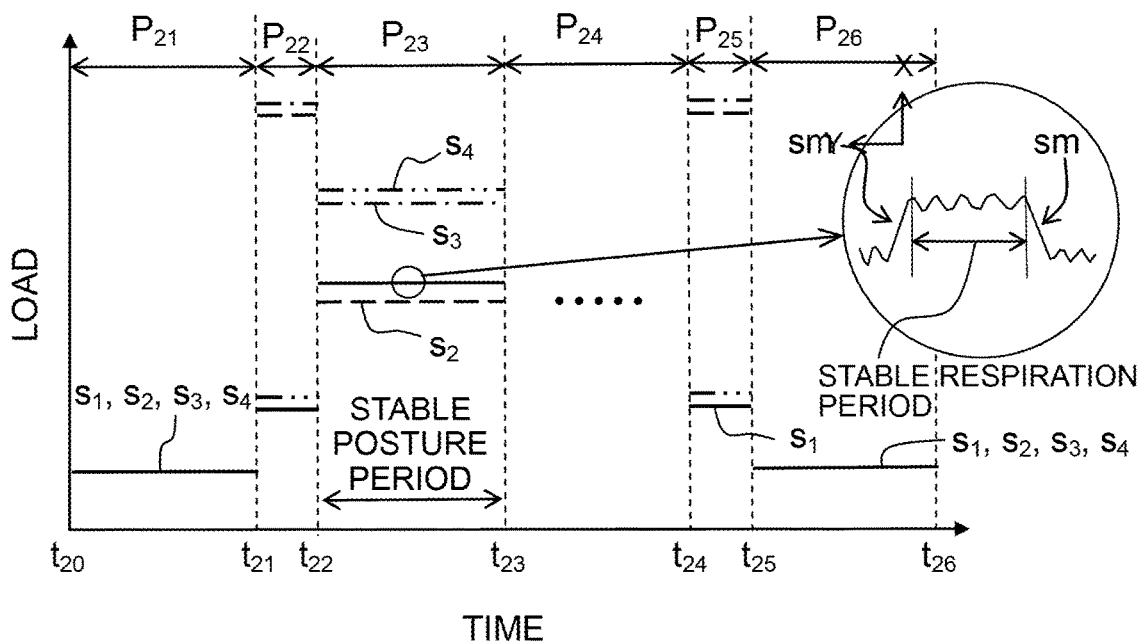
FIG. 14B depicts exemplary load signals fed from load detectors as detected in the load detecting step according to the modified embodiment.

Exemplary load signals detected in the load detecting step S201 are depicted in FIG. 14B. FIG. 14B shows the load signals $s_1$ (solid line), $s_2$ (broken line), $s_3$ (alternate long and short dash line), and $s_4$ (alternate long and two short dashes line) from the load detectors 11, 12, 13, 14, respectively, outputted during the period ranging from the time $t_{20}$ to the time $t_{26}$. The load detectors 11 to 14 are provided in the areas I to IV depicted in FIG. 4 respectively in the same manner as in the embodiment described above. The following fact has been observed. That is, the subject S was absent on the bed BD during the period (period $P_{21}$) ranging from the time $t_{20}$ to the time $t_{21}$. The subject S sat down on the side of the areas II, III of the bed BD at the time $t_{21}$, and then the subject S took such a position that the subject S lay on his/her back at the center of the bed BD at the time $t_{22}$. Further, the following fact has been observed. That is, the subject S took arbitrary postures during the period (period $P_{24}$) ranging from the time $t_{23}$ to the time $t_{24}$, and then the subject S sat down on the side of the areas II, III of the bed BD again at the time $t_{24}$. After that, the subject S left the bed BD at the time $t_{25}$.

The subject S is absent on the bed BD during the period $P_{21}$. Therefore, all of the signals $s_1$ to $s_4$ fed from the load detectors 11 to 14 are equal to one another during the period $P_{21}$, and each of them exhibits the load value corresponding to about ¼ of the weight of the bed BD.

The signals $s_1$ to $s_4$ fed from the load detectors 11 to 14 greatly change at the time $t_{21}$ at which the subject S is seated in the areas II, III of the bed BD. Specifically, each of the signals $s_1$ to $s_4$ is increased at the time $t_{21}$. The amount of increase in the load value of the signal $s_2$, $s_3$ fed from the load detector 12, 13 corresponding to the area II, III is larger than the amount of increase in the load value of the signal $s_1$, $s_4$ fed from the load detector 11, 14 corresponding to the area I, IV. Note that in this section, it is assumed that the subject S seated on the bed BD has feet separated from the floor and the entire body weight of the subject S is applied onto the bed BD for convenience of the explanation.

In the load detecting step S201, the large increase in the total value of the load values of the signals $s_1$ to $s_4$ as generated at the time $t_{21}$ is detected by the center of gravity position calculating unit 31 (bed-leaving/settling judging unit), and it is judged that the subject S is settled on the bed BD on the basis of the detection. The result of judgment may be displayed on the display unit 5.

The judgment of the settling of the subject S on the bed BD, which is performed by the center of gravity position calculating unit 31, may be made, for example, depending on whether or not the increase in the total value of the load values indicated by the signals $s_1$ to $s_4$ fed from the load detectors 11 to 14 exceeds a predetermined value (the value is, for example, 40 kg, 55 kg, or 70 kg, and the value can be arbitrarily set by using, for example, input unit 7).

The subject S, who is seated in the areas II, III of the bed BD at the time $t_{21}$, greatly changes the posture so that the subject S lies on his/her back at the central portion of the bed BD at the time $t_{22}$. Therefore, the signals $s_1$ to $s_4$ fed from the load detectors 11 to 14 also greatly change at the time $t_{22}$. The load values of the signals $s_2$, $s_3$ corresponding to the area II and the area III are decreased, and the load values of the signals $s_1$, $s_4$ corresponding to the area I and the area IV are increased.

The subject S lies on his/her back at the central portion of the bed BD during the period $P_{23}$. Therefore, during the period $P_{23}$, the signals $s_3$, $s_4$ fed from the load detectors 13, 14 arranged on the head side of the subject S are approximately equal to one another, and the signals $s_1$, $s_2$ fed from the load detectors 11, 12 arranged on the foot side of the subject S are approximately equal to one another. In this modified embodiment, the period, in which the subject S takes the stable posture on the bed BD and any large body motion of the subject S does not occur as described above, is referred to as "stable posture period".

Further, as depicted in the enlarged part depicted in FIG. 14B, each of the signals $s_1$ to $s_4$ fed from the load detectors 11 to 14 always varies minutely resulting from, for example, the respiration of the subject S during the stable posture period as well, and each of the signals $s_1$ to $s_4$ sporadically varies on account of the small body motion of the subject S (variation sm depicted in the enlarged part of FIG. 14B). In this modified embodiment, the period included in the "stable posture period", in which only the variations of the signals $s_1$ to $s_4$ caused, for example, by the respiration occur and the variations of the signals $s_1$ to $s_4$ caused by the small body motion do not occur, is referred to as "stable respiration period". The calculation of, for example, the respiration and the heart beat described later on can be performed especially satisfactorily during the stable respiration period.

The signals $s_1$ to $s_4$, which are provided during the period $P_{25}$ in which the subject S sits down in the areas II, III of the bed BD again, are the same as the signals $s_1$ to $s_4$ which are provided during the period $P_{22}$.

The load value of each of the signals $s_1$ to $s_4$ fed from the load detectors 11 to 14 is lowered at the time $t_{25}$ at which the subject S leaves the areas II, III of the bed BD. The load value of each of the signals $s_1$ to $s_4$ provided during the period $P_{26}$ thereafter is equal to the value provided during the period $P_{21}$ in which only the load value corresponding to about ¼ of the weight of the bed BD is exhibited.

In the load detecting step S201, the large decrease in the total of the load values of the signals $s_1$ to $s_4$ as generated at the time $t_{25}$ is detected by the center of gravity position calculating unit 31. It is judged on the basis of the detection that the subject S has left the bed BD. The judgment result may be displayed on the display unit 5.

The period, which ranges until the center of gravity position calculating unit 31 detects the leaving of the subject S from the bed BD after the detection of the settling of the subject S on the bed BD, is referred to as "settling period" in this modified embodiment (FIG. 14A). In this modified embodiment, various types of filtering are applied to the center of gravity locus of the subject S which is obtained during the settling period to acquire the biometric information such as the respiratory rate of the subject S.

In the load detecting step S201, it is possible to measure the body weight of the subject S at any single point in time or a plurality of points in time of the settling period by using the center of gravity position calculating unit 31 (body weight measuring unit). The body weight of the subject S can be acquired by subtracting the weight of the bed BD previously stored in the storage unit 4 from the total value of the load values of the signals $s_1$ to $s_4$.

Respiratory Rate Calculating Step

In the respiratory rate calculating step S203, the process contents of the large body motion determining step S2031 and the process contents of the small body motion determining step S2032 are different from the process contents of the large body motion determining step S1031 and the process contents of the small body motion determining step S1032 included in the respiratory rate calculating step S103. Detailed procedures of the respiratory rate calculating step S203 will be explained as exemplified by a case in which the respiratory rate per one minute is calculated.

Figure 15B:
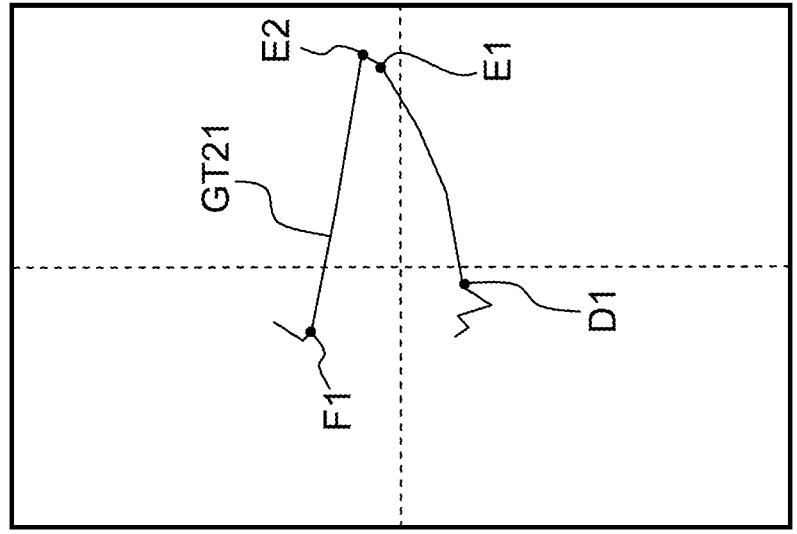
FIG. 15B depicts a locus of the center of gravity obtained by converting the locus of the center of gravity depicted in FIG. 15A into the locus based on a low sampling frequency.
Figure 15A:
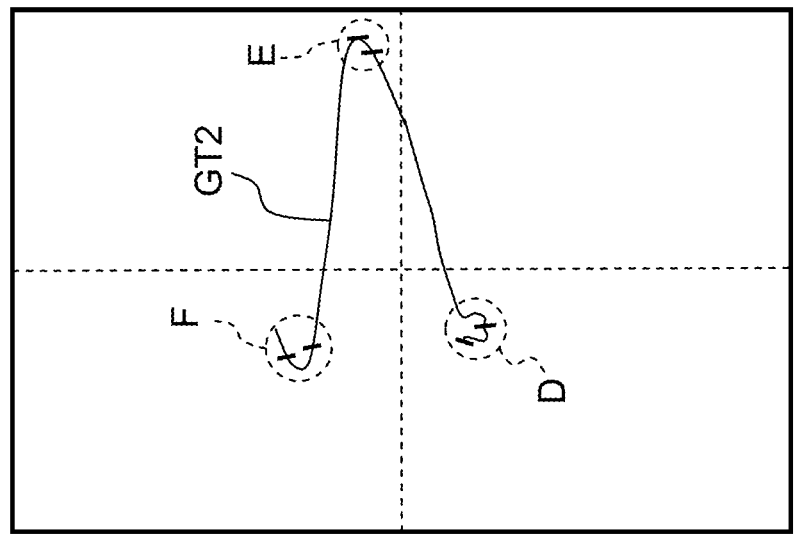
FIG. 15A depicts another exemplary locus of the center of gravity of a subject.

At first, the body motion information determining unit 37 extracts, from the storage unit 4, the center of gravity locus GT2 of the subject S per one minute included in the settling period. An example of the extracted center of gravity locus GT2 is depicted in FIG. 15A. The center of gravity locus GT2 depicted in FIG. 15A indicates the fact that the subject S makes one reciprocating motion in the left-right direction on the bed in accordance with the large body motion (turning over or the like). Further, the center of gravity locus GT2 indicates that the center of gravity G of the subject S moves in each of the areas D, E, F during the stable posture period in which no large body motion occurs. The movement of the center of gravity G in the areas D, E, F is caused, for example, by the respiration and the small body motion of the subject S.

The large body motion information determining unit (first body motion information determining unit) 37A, which is included in the body motion information determining unit 37, determines and extracts the locus of the center of gravity movement caused by the large body motion of the subject S from the center of gravity locus GT2 (large body motion determining step S2031). The large body motion information determining unit 37A judges that the large body motion has occurred if the center of gravity G moves in a certain direction within a certain time period beyond a certain distance, for example, if the center of gravity G moves from one area to another area within a certain time. The large body motion information determining unit 37A extracts the center of gravity locus GT2 provided during this period.

In the large body motion determining step S2031, it is judged whether or not the center of gravity G moves in a certain direction within a certain time period beyond a certain distance, by using the following method. At first, the center of gravity locus GT2 depicted in FIG. 15A is converted into a center of gravity locus GT21 based on a lower sampling frequency (FIG. 15B). The conversion can be performed by thinning out the data of the center of gravity position G acquired at a sampling frequency of 0.1 second and/or by using the moving average process. Alternatively, the conversion can be also performed by subjecting the center of gravity locus GT2 to the frequency resolution and extracting the predetermined low frequency component by means of a low-pass filter.

With reference to FIG. 15B, the locus between the point D1 and the point E1 exhibits, for example, the movement in the right direction within 0.5 second beyond 30 cm. Therefore, the respiratory rate calculating unit 32 judges that the locus in this interval is the locus of the large body motion.

The respiratory rate calculating unit 32 removes the locus in this interval from the center of gravity locus GT2. Similarly, the locus between the point E2 and the point F1 exhibits, for example, the movement in the left direction within 0.5 second beyond 30 cm. Therefore, the large body motion information determining unit 37A judges that the locus in this interval is the locus of the large body motion. The large body motion information determining unit 37A removes the locus in this interval from the center of gravity locus GT2. Note that the movement from the point D1 to the point E1 and the movement from the point E2 to the point F1 may be identified as the movements related to the large body motion on the basis of the fact that each movement is a movement from one area to another area.

Figure 16A:
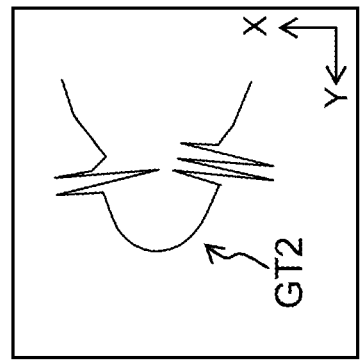
FIG. 16A depicts locus obtained by removing the locus of the movement of the center of gravity caused by the large body motion of the subject from the locus of the center of gravity of the subject on the bed depicted in FIG. 15A.
Figure 16B:
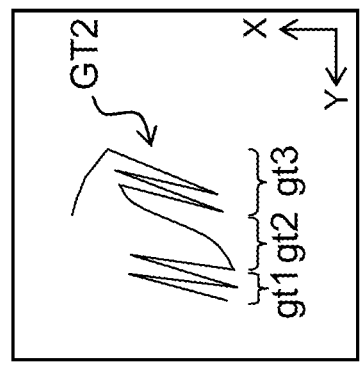
FIG. 16B depicts locus obtained by removing the locus of the movement of the center of gravity caused by the large body motion of the subject from the locus of the center of gravity of the subject on the bed depicted in FIG. 15A.
Figure 16C:
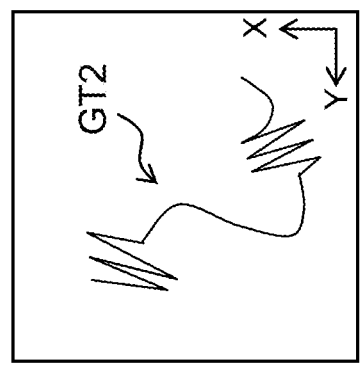
FIG. 16C depicts locus obtained by removing the locus of the movement of the center of gravity caused by the large body motion of the subject from the locus of the center of gravity of the subject on the bed depicted in FIG. 15A.

The loci, obtained by removing the locus of the large body motion from the center of gravity locus GT2 depicted in FIG. ISA, are depicted in FIGS. 16A to 16C. FIG. 16A depicts the center of gravity locus GT2 in the area D, FIG. 16E depicts the center of gravity locus GT2 in the area E, and FIG. 16C depicts the center of gravity locus GT2 in the area F. Each of the loci is the center of gravity locus GT2 during the stable posture period.

Note that it is desirable that the low sampling frequency has the period which is short (the frequency which is large) to such an extent that the large body motion is sufficiently extracted, and the low sampling frequency has the period which is long (frequency which is small) to such an extent that no influence is exerted by the variation of the center of gravity caused by any other factor than the large body motion such as the small body motion, the respiration or the like. Further, the extent of the time and the extent of the distance, on the basis of which it is to be judged that the large body motion is caused when the movement occurs within that time by that distance, can be optimized in conformity with the feature of the apparatus of the biometric information monitoring system 200.

Subsequently, the small body motion information determining unit (second body motion information determining unit) 37B of the body motion information determining unit 37 determines and extracts the locus of the center of gravity movement caused by the small body motion of the subject S from the center of gravity locus GT2 during the stable posture period (small body motion determining step S2032). The step of removing the locus of the center of gravity movement caused by the small body motion of the subject S from the center of gravity locus GT2 during the stable posture period will be explained. Here, a procedure in which the small body motion locus and the respiration locus are separated from the center of gravity locus GT2 in the area E (FIG. 16B) will be explained as an example.

In the small body motion determining step S2032, the center of gravity locus, which is calculated by the respiratory rate calculating unit 32 using data of past measurement, and which oscillates periodically in specified directions, is identified as the center of gravity locus based on the respiration. The center of gravity locus, which is different from the center of gravity locus as identified above, is regarded as the center of gravity locus based on the small body motion.

With reference to FIG. 16B, the center of gravity locus GT2 includes the portions gt1, gt3 which represent the movement of the center of gravity G caused by the respiration and the portion gt2 which represents the movement of the center of gravity G caused by the small body motion (note that the portion gt2 represents the movement of the center of gravity G caused by the respiration as well). The portion gt2, which represents the movement of the center of gravity G caused by the small body motion, does not periodically oscillate in any specified direction, unlike the center of gravity loci of the portions gt1, gt3 which represent the movement of the center of gravity G caused by the respiration.

Therefore, one method is available to separate and extract the locus of the center of gravity movement caused by the small body motion. That is, only the center of gravity locus (gt1, gt3), which oscillates periodically in specified directions, is extracted, and it is regarded as the respiratory component of the center of gravity movement. Then, the other portion (gt2) is separated and extracted as the small body motion. The separation and the extraction as described above, for example, can be carried out in accordance with the method as described below. The center of gravity variation, which is repeated periodically and which is included in the center of gravity variations provided during a past certain period in the stable respiration phase, is detected by means of the frequency analysis such as the Fourier analysis or the like. The direction of the center of gravity change exhibited in the corresponding frequency is detected, and this is regarded as the center of gravity variation caused by the respiration. After that, the difference between the presently measured center of gravity variation and the center of gravity variation caused by the respiration is extracted as the variation caused by the small body motion. In this procedure, if the component having the corresponding frequency is not included in the presently measured center of gravity variation and/or the amplitude of the presently measured center of gravity variation has largely changed, then it is regarded that the respiration condition of the subject S has changed, and obtaining the difference by using the center of gravity variation caused by the respiration is not performed.

Figure 18:
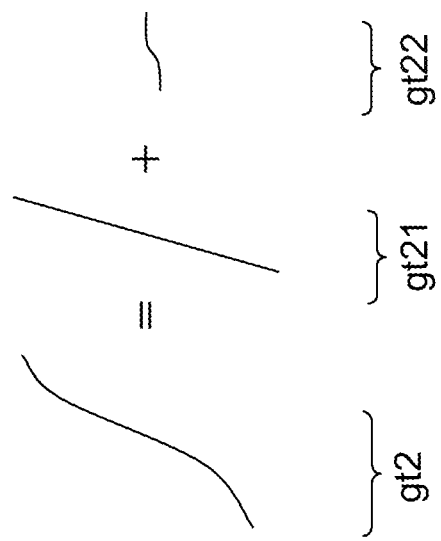
FIG. 18 depicts the component of respiration extracted from the locus of the center of gravity depicted in FIG. 16B.
Figure 17:
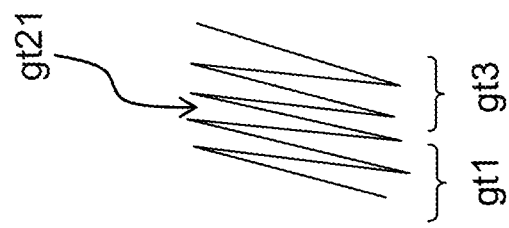
FIG. 17 depicts decomposition of the locus of the center of gravity into the component of the respiration and the component of the small body motion.

Another method is available as depicted in FIG. 17. That is, the portion (gt2), which does not form the center of gravity locus oscillating periodically in any specified direction, is decomposed into the portion gt21 which constitutes a part of the center of gravity locus oscillating periodically in a specified direction and the other portion gt22. Then, only the portion gt21, which constitutes the part of the center of gravity locus oscillating periodically in the specified direction, is returned to the position between the portion gt1 and the portion gt3 to acquire the center of gravity locus as depicted in FIG. 18. This is used as the respiratory component of the center of gravity movement. Meanwhile, the portion gt22, which is decomposed from the portion gt2, is separated and extracted as the small body motion. The separation and the extraction as described above can be carried out in accordance with the foregoing method.

After that, the respiratory component of the center of gravity movement extracted by the body motion information determining unit 37 is fed to the respiratory rate calculating unit 32. In the respiratory rate calculating unit 32, the respiratory rate is calculated by the same or equivalent means as that used in the embodiment described above. Note that it is also appropriate that the body motion information determining unit 37 determines only the locus of the center of gravity movement caused by the large body motion and the locus of the center of gravity movement caused by the small body motion. That is, it is not necessarily indispensable to separate and extract the loci caused by the large and small body motions from the center of gravity locus. In this case, for example, the respiratory rate calculating unit 32 extracts the respiratory component from the center of gravity locus with reference to the locus of the center of gravity movement caused by the large body motion and the locus of the center of gravity movement caused by the small body motion each of which was determined by the body motion information determining unit 37.

The steps of this modified embodiment can be also carried out by using the biometric information monitoring system 100 of the embodiment described above. In this case, the step, which is performed by the body motion information determining unit 37, can be performed by the respiratory rate calculating unit 32. On the contrary, the steps of the embodiment described above can be also carried out by using the biometric information monitoring system 200 of this modified embodiment. In this case, the large body motion determining step S1031 may be performed by the large body motion information determining unit 37A, and the small body motion determining step S1032 may be performed by the small body motion information determining unit 37B.

It is also possible to adopt the following modified embodiments in the biometric information monitoring system 100 of the embodiment described above.

In the biometric information monitoring system 100 of the embodiment described above, the heart rate is calculated by extracting the signal component in the frequency band of 0.5 Hz to 2.5 Hz corresponding to the heart rate component from the output values of the four load detectors 11 to 14. However, there is no limitation thereto. The heart rate has the unique period in which a plurality of center of gravity variations are combined, and thus, the heart rate calculating unit 34 can estimate the displacement of the center of gravity considered to be caused by the present heart beat on the basis of the past calculation result. Therefore, the locus caused by the heart beat can be extracted from the center of gravity locus on the basis of the estimated displacement of the center of gravity, and the heart rate can be determined on the basis of the extracted locus.

The physical condition judging unit 36 of the biometric information monitoring system 100 of the embodiment described above judges the sleep/wakefulness of the subject S on the basis of the values of the respiratory ventilation volume and the respiratory rate of the subject S. However, there is no limitation thereto. For example, the result of another system, which can be used as a reference data for judging the wakefulness/sleep, may be used as the teacher data. Alternatively, the data, which is labeled in relation to the condition of the subject in accordance with a camera or a decision or judgment of a doctor, may be used as the teacher data.

The physical condition judging unit 36 judges the physical condition of the subject by integrally using the data of various types of biometric information (for example, body weight, body motion, respiration, and heart beat). In this procedure, in order to raise the accuracy in judging the physical condition, it is also allowable to perform the machine learning based on the use of the teacher data. That is, the function for judging whether the subject S is a sleep state or a wakeful state is previously prepared by means of the fitting from a large number of pieces of biometric information (labeled teacher data), and the data of various types of biometric information, which is obtained from the biometric information monitoring system 100 of this embodiment, is substituted into the function so as to acquire the physical condition (i.e. the sleep or the wakefulness). That is, the algorithm of sleep/wakefulness can be obtained by the machine learning based on the use of various types of biometric information such as the leaving from the bed, the settling on the bed, the large body motion, the small body motion, the respiration, the apnea, the snore, the utterance, and the heart beat and the operation thereof (mathematical analysis including, for example, the four arithmetic operations, the integration, the differentiation, and the frequency analysis), as obtained from the biometric information monitoring system 100 with reference to the teacher data labeled as "during the wakefulness" or "during the sleep" sampled from the subject.

The physical condition judging unit 36 of the biometric information monitoring system 100 of the embodiment described above can also detect the fall of the subject S from the bed BD. Specifically, the physical condition judging unit 36 can judge that the subject S has fallen from the bed BD if the large body motion and the leaving from the bed (or only the leaving from the bed) occur (occurs) when the subject S is in the sleep state. Further, the judgment result may be displayed on the display unit 5. The judgment result may be notified to the user of the biometric information monitoring system 100 by using the notifying unit 6. Note that the physical condition judging unit 36 may judge that the subject S has left the bed in accordance with his/her own intention if the large body motion and the leaving from the bed occur when the subject S is in the wakeful state.

The physical condition judging unit 36 of the biometric information monitoring system 100 of the embodiment described above may judge whether the subject S is alive or dead on the basis of various types of biometric information acquired by the biometric information monitoring system 100. Specifically, for example, the physical condition judging unit 36 can judge that the subject S is dead if all of the body motion of the subject S (large body motion and small body motion acquired from the movement of the center of gravity G), the respiration, and the heart beat stop under a certain condition. The certain condition can be set on the basis of the judgment of a doctor or the like as the user.

The physical condition judging unit 36 of the biometric information monitoring system 100 of the embodiment described above can also judge that the subject in the apnea condition which is a symptom of the sleep apnea syndrome. If a patient of the sleep apnea syndrome falls into the apnea during the sleep, then the respiration and the body motion stop during a certain period, and then inhalation is performed greatly to cause the respiration and the body motion. On the other hand, the heart beat continues throughout the above period. Therefore, the physical condition judging unit 36 can detect that the apnea condition has occurred if the period, in which the respiration and the body motion stop and the heart beat continues, continues for not less than a certain time period.

The physical condition judging unit 36 may display the judgment result on the display unit 5. The judgment result may be notified to the user of the biometric information monitoring system 100 by using the notifying unit 6 (nurse call). Further, the physical condition judging unit 36 may label the biometric information corresponding to the period in which the apnea condition occurred, when storing various types of measured biometric information in the storage unit 4. With this, it is made easier to observe the symptom of the sleep apnea syndrome of the subject S after the event (ex post fact).

The physical condition judging unit 36 of the biometric information monitoring system 100 of the embodiment described above can also detect the utterance and the snore of the subject S. In general, the utterance is performed simultaneously with the expiration. Therefore, for example, if any high frequency component is generated in the expiration period during the wakefulness or the sleep, it is possible to judge that the high frequency component is caused by the utterance. On the other hand, the snore generally occurs during the inhalation. Therefore, for example, if any high frequency component is generated in the inhalation period during the sleep, it is possible to judge that the high frequency component is caused by the snore.

When the center of gravity locus exhibits the movement which is different from the ordinary movement, then the notifying unit 6 of the biometric information monitoring system 100 of the embodiment described above may regard the movement as abnormal movement, and the notifying unit 6 may perform the notification by using the notifying unit 6 (nurse call). It is possible to appropriately set what kind of movement is the "movement different from the ordinary movement". As an example, if a predetermined large body motion or a small body motion continues for not less than a certain time period in a successive manner, n it is possible to judge that the "movement different from the ordinary movement" has occurred, and to perform the nurse call based on the judgement. When the nurse call signal is received, it is also allowable to operate a camera which captures the situation of the bed.

Figure 19:
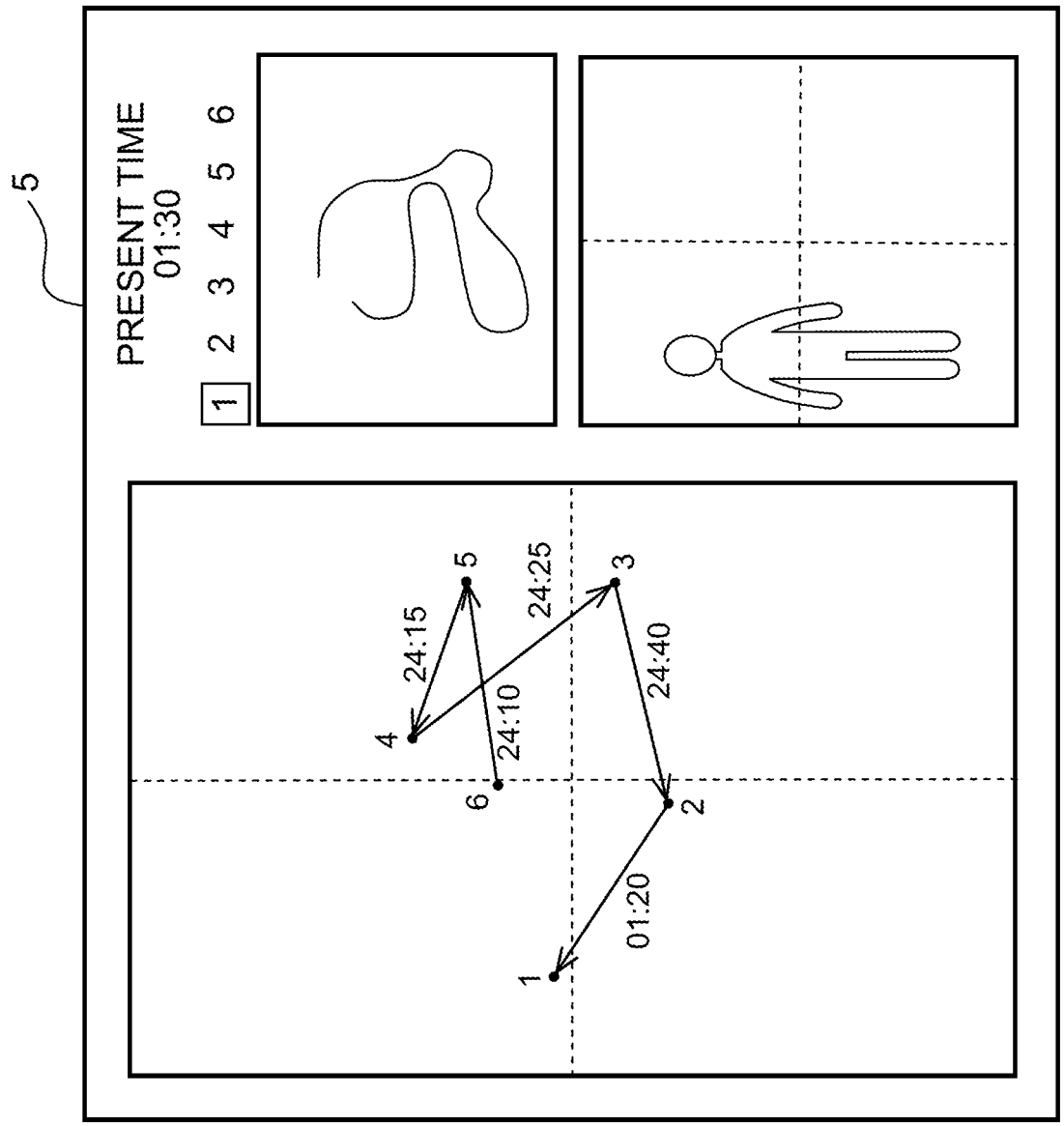
FIG. 19 depicts an exemplary display screen of a display unit 5.

In the biometric information monitoring system 100 of the embodiment described above, the large body motion extracted in the large body motion determining step S1031, S2031 and the small body motion extracted in the small body motion determining step S1032, S2032 may be displayed on the display unit 5. Specifically, for example, as depicted in FIG. 19, it is possible to display the locus of the large body motion and the locus of the small body motion on a screen area which is designed to imitate the upper surface of the bed. When the history of the large body motion is displayed together with the time, the user such as a doctor or the like can thereby easily grasp the outline of the behavior of the subject S during the sleep.

In the embodiment described above, the period, which is provided between one large body motion and another large body motion, is defined as the "stable posture period", and the respiratory component and the component of the small body motion of the center of gravity locus are extracted from the locus corresponding to the stable posture period. However, the following fact has been observed. That is, the center of gravity of the subject S is not stable, and a relatively large variation of the center of gravity position occurs immediately before the large body motion occurs and immediately after the large body motion has occurred. Therefore, by extracting the respiratory component and the component of the small body motion only from the center of gravity locus provided during the period obtained by further removing, from the "stable posture period", certain periods provided immediately before and immediately after the large body motion, it is possible to more correctly acquire the biometric information such as the respiratory rate or the like.

In the embodiment described above, the leaving from the bed and the settling on the bed of the subject S are judged on the basis of the total of the load values of the signals $s_1$ to $s_4$ fed from the load sensors 11 to 14. However, there is no limitation thereto. With reference to FIG. 14B, the load from the bed BD is equally applied to the load sensors 11 to 14 during the period $P_{21}$ in which the subject S is absent on the bed. In other words, the center of gravity G is positioned at the center of the bed BD. When the subject S is settled on the bed BD at the time $t_{21}$, the center of gravity G is greatly moved to the side of the areas II, III. The center of gravity position calculating unit 31 can judge the settlement of the subject S on the bed on the basis of the large movement of the center of gravity G as described above. The leaving of the subject S from the bed can be also judged in the same manner as described above.

In the embodiment described above, the direction, in which the body axis of the subject S extends, is acquired by acquiring the direction of the mode vector $v_f$ by the respiratory rate calculating unit 32. However, it is also allowable to acquire the direction by any means or any processing unit distinct from the respiratory rate calculating unit 32.

In the embodiment described above, the respiratory rate calculating unit 32 is used to separate and extract the body motion information relevant to the large body motion (first information) and the body motion information relevant to the small body motion (second information). However, there is no limitation thereto. The body motion information relevant to the large body motion may be separated and extracted by any means (for example, a large body motion information deriving unit) distinct from the respiratory rate calculating unit 32, and similarly, the body motion information relevant to the small body motion may be separated and extracted by any means (for example, a small body motion information deriving unit) distinct from the respiratory rate calculating unit 32.

In the biometric information monitoring system 100 of the embodiment described above, the respiratory rate calculating unit 32 calculates the respiratory rate of the subject S by using the wavelet transformation. However, it is also possible to use any other method. Specifically, for example, the point positioned on the most positive side in the X axis direction and the point positioned on the most negative side in the X axis direction are firstly acquired from the center of gravity locus GT depicted in FIG. 12 to calculate the intermediate value Xm of the X coordinates of the both points. As depicted in FIG. 12, the intermediate value Xm can be regarded as the center of oscillation of the center of gravity locus GT caused by the respiration of the subject S. Subsequently, the respiratory rate calculating unit 32 acquires the number of times of movement of the center of gravity locus GT from the negative side to the positive side (or the positive side to the negative side) in the X axis direction while crossing over the intermediate value Xm. Based on the acquired number of times, the respiratory rate calculating unit 32 calculates the frequency of the center of gravity locus GT caused by the respiration of the subject S, i.e., the respiratory rate.

Note that in the embodiment described above, each of the load detectors 11, 12, 13, 14 is not limited to the load sensor having the beam-type load cell. It is also possible to use, for example, a force sensor.

Note that in the embodiment described above, the number of load detectors is not limited to four. It is also allowable to use five or more load detectors by providing an additional foot or additional feet for the bed BD. Alternatively, it is also allowable to arrange the load detectors for only three of the feet of the bed BD. Even when the three load detectors are used, it is possible to detect a position of the center of gravity G of the subject S on the plane of the bed BD provided that the three load detectors are not arranged on a straight line.

Figure 20:
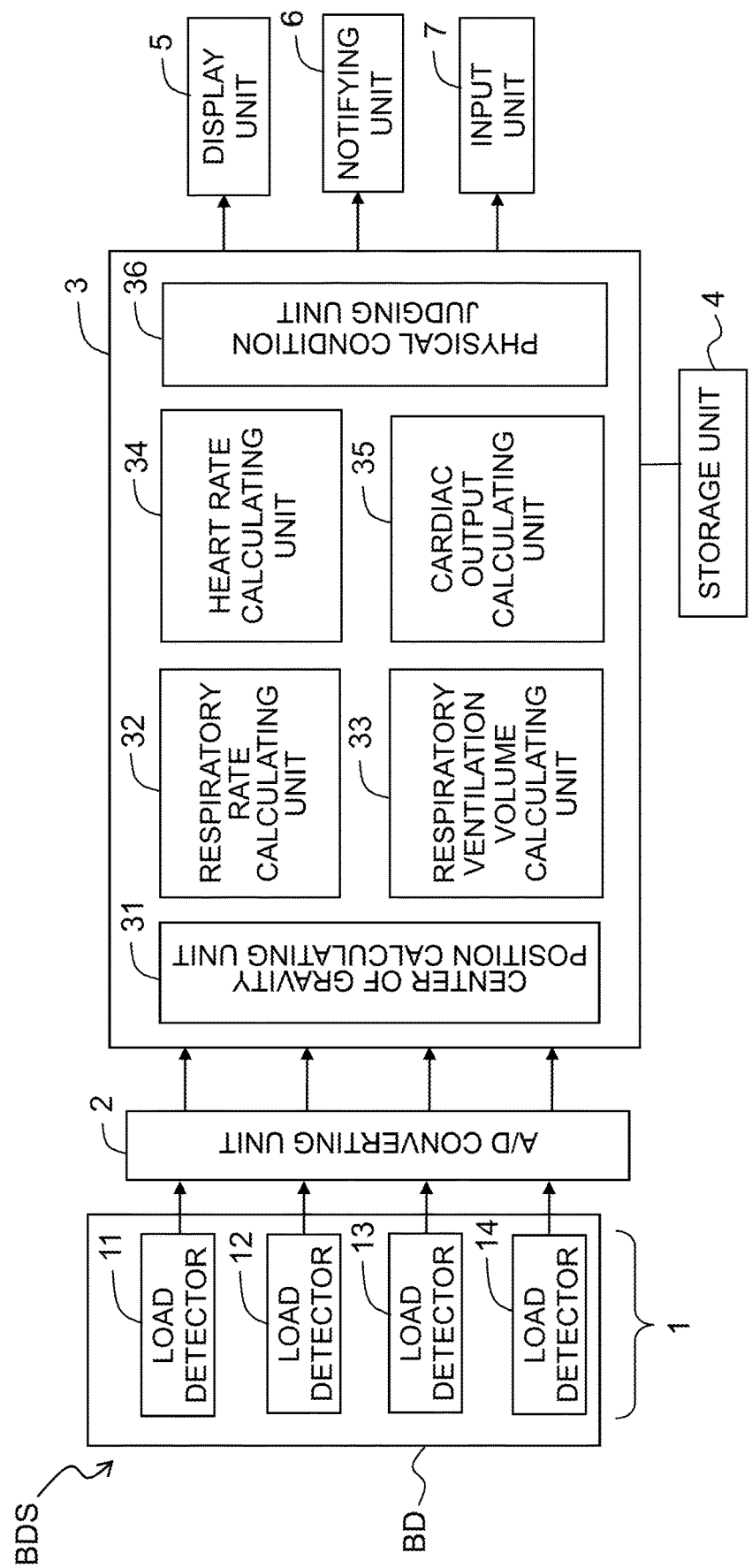
FIG. 20 is a block diagram depicting an overall configuration of a bed system according to an embodiment of the present disclosure.

Note that in the embodiment described above, the load detectors 11, 12, 13, 14 are arranged respectively under the casters $C_1$, $C_2$, $C_3$, $C_4$ attached to the lower ends of the feet of the bed BD. However, there is no limitation thereto. Each of the load detectors 11, 12, 13, 14 may be provided respectively between one of the four feet of the bed BD and the board of the bed BD. Alternatively, if each of the four feet of the bed BD can be divided into upper and lower portions, each of the load detectors 11, 12, 13, 14 may be provided between upper foot and lower foot. Further alternatively, the load detectors 11, 12, 13, 14 may be formed integrally with the bed BD to construct a bed system BDS comprising the bed BD and the biometric information monitoring system 100 of this embodiment (FIG. 20). Note that in this specification, the "load detectors placed in the bed" mean the load detectors each of which is provided between one of the four feet of the bed BD and the board of the bed BD as described above and the load detectors each of which is provided between the upper foot and the lower foot.

Note that in the embodiment described above, it is also allowable to provide a signal amplifying unit for amplifying the load signal fed from the load detecting unit 1 and/or a filtering unit for removing the noise from the load signal, between the load detecting unit 1 and the A/D converting unit 2.

Note that in the biometric information monitoring system 100 of the embodiment described above, the display unit 5 is not limited to the unit which displays the information on the monitor so that the user can make the visual recognition. For example, the display unit 5 may be a printer which periodically prints and outputs the respiratory condition (respiratory rate, respiratory ventilation volume), the state of the heart beat, and the physical condition of the subject S. Alternatively, the display unit 5 may be a unit which performs the display by using any simple visual expression, for example, such that a blue lamp is turned ON in the case of the sleep state, a yellow lamp is turned ON in the case of the wakeful state, and/or a red lamp is turned ON in the case of the apnea condition. Further alternatively, the display unit 5 may be a unit which reports the respiratory condition and the physical condition of the subject S to the user by means of any sound or voice. Further alternatively, it is also allowable that the biometric information monitoring system 100 does not have the display unit 5. The biometric information monitoring system 100 may have only an output terminal for outputting the information. A monitor (display device) or the like, which is provided to perform the display, will be connected to the biometric information monitoring system 100 by the aid of the output terminal.

Note that the notifying unit 6 of the embodiment described above performs the notification auditorily. However, the notifying unit 6 may be constructed to perform the notification visually by means of, for example, the flashing or flickering of light. Alternatively, the notifying unit 6 may be constructed to perform the notification by means of the vibration. Further, it is also allowable that the biometric information monitoring system 100 of the embodiment described above does not have the notifying unit 6.

Note that the components of the biometric information monitoring system 100 of the embodiment described above, which are connected to one another by means of the wirings, may be connected to one another in a wireless manner.

In the embodiment described above, the body weight is measured by the center of gravity position calculating unit 31. However, it is also allowable to distinctly provide a body weight measuring unit in the control unit 3.

In the biometric information monitoring system of the present disclosure, the second body motion information determining unit determines the small body motion based on the temporal variation of the center of gravity position from which the large body motion determined by the first body motion information determining unit has been removed. However, in addition thereto or in place thereof, it is also allowable to determine the small body motion on the basis of the direction of movement of the center of gravity position and/or the periodicity based on the influence of the respiration.

The biometric information monitoring system of the present disclosure can synchronously acquire not only the large body motion information, the small body motion information, and the respiratory rate, but also the body weight, the heart beat, and the judgement result of the physical condition judging unit.

The physical condition judging unit of the biometric information monitoring system of the present disclosure may judge not only whether the subject is in the sleep state or the wakeful state but also whether or not the subject is in the delirium state, on the basis of the acquired body motion information and/or the respiratory rate of the subject.

The bed-leaving/settling judging unit of the biometric information monitoring system of the present disclosure may judge not only whether or not the subject is present on the bed but also the body weight and/or the body weight variation of the subject on the basis of the detected load.

The display unit of the biometric information monitoring system of the present disclosure may display the present states and the temporal changes of the acquired body motion information, the body axis direction, the respiration, and the heart beat of the subject as the history of movement of the center of gravity position on the bed.

The present invention is not limited to the embodiments described above provided that the feature of the present invention is maintained. Other embodiments, which are conceivable within the scope of the technical concept of the present invention, are also included in the scope of the present invention.

In the biometric information monitoring system according to the above embodiments, the body motion information determining unit may include a first body motion information determining unit which determines information on a large body motion of the subject and a second body motion information determining unit which determines information on a small body motion of the subject.

In the biometric information monitoring system according to the above embodiments, the first body motion information determining unit may determine a variation caused by the large body motion of the subject included in the temporal variation of the center of gravity position of the subject, based on a movement distance of the center of gravity position within a predetermined time period.

In the biometric information monitoring system according to the above embodiments, the second body motion information determining unit may determine a variation, caused by the small body motion of the subject, included in the temporal variation of the center of gravity position of the subject, based on a movement direction of the center of gravity position, the temporal variation of the center of gravity position being a variation from which the variation caused by the large body motion determined by the first body motion information determining unit has been removed.

In the biometric information monitoring system according to the above embodiments, the respiratory rate calculating unit may calculate the respiratory rate based on the temporal variation of the center of gravity position of the subject from which the variation caused by the large body motion determined by the first body motion information determining unit and the variation caused by the small body motion determined by the second body motion information determining unit have been removed.

In the biometric information monitoring system according to the above embodiments, the information on the large body motion, the information on the small body motion, and the respiratory rate may be synchronously acquired.

The biometric information monitoring system according to the above embodiments may further comprise a physical condition judging unit which judges whether the subject is in a sleep state or a wakeful state based on the acquired information on the body motion of the subject and/or the respiratory rate of the subject.

The biometric information monitoring system according to the above embodiments may further comprise a bed-leaving/settling judging unit which judges whether or not the subject is present on the bed based on the detected load; and the physical condition judging unit may judge that the subject has fallen from the bed in a case that the subject is judged to be in the sleep state by the physical condition judging unit and is judged to have left the bed by the bed-leaving/settling judging unit.

The biometric information monitoring system according to the above embodiments may further comprise a heart rate calculating unit which acquires a heart rate of the subject based on the acquired temporal variation of the center of gravity position of the subject.

In the biometric information monitoring system according to the above embodiments, the physical condition judging unit may judge whether the subject is alive or dead based the acquired information on the body motion, the respiratory rate, and the heart rate of the subject.

The biometric information monitoring system according to the above embodiments may further comprise a display unit which displays a temporal variation of the acquired information on the body motion of the subject as a history of movement of the center of gravity position on the bed The biometric information monitoring system according to the above embodiments may further comprise a notifying unit which performs notification based on the acquired temporal variation of the center of gravity position of the subject.

In the biometric information monitoring system according to the above embodiments, the temporal variation of the center of gravity position may include a variation caused by the body motion of the subject and a variation caused by respiration of the subject, and the biometric information monitoring system may further comprise a body axis determining unit which acquires a body axis of the subject based on the variation caused by the respiration.

The biometric information monitoring system according to the above embodiments may further comprise a body weight measuring unit which acquires a body weight of the subject based on the detected load.

The biometric information monitoring system using the bed sensor of one aspect of the present disclosure, can provide the monitoring system, which is the noninvasive sensor, and which makes it possible to monitor the biometric information of the subject at a high accuracy without giving any discomfort and any unpleasantness to the subject. Further, the biometric information monitoring system using the bed sensor of one aspect of the present disclosure, makes it possible to simultaneously and synchronously measure the states of the biometric information including, for example the body weight, the body motion, the respiration, the snore, and the heart beat and the temporal changes thereof from the time series data of the load sensors. Therefore, the physical condition of the subject, which changes in time series, can be also judged in synchronization with the biometric information at the respective times.

According to the biometric information monitoring system of one aspect of the present disclosure, it is possible to quantitatively measure the respiratory rate and the ventilation volume of the respiration based on the positional change of the center of gravity, and it is possible to continuously monitor the respiratory condition of an inpatient in the noninvasive and noncontact manner. Further, according to the biometric information monitoring system of one aspect of the present disclosure, it is possible to synchronously detect the body motion information and the respiration information, such as the respiratory rate or the like, as well as the inspection items including, for example, the body weight, the heart rate, the snore, and occurrence of the leaving from the bed and the settling on the bed, by using only the load detectors placed under the bed or in the bed. Therefore, it is unnecessary to attach different sensors to the subject for the respective items, and it is unnecessary to synchronize the outputs from a plurality of sensors. Further, it is possible to automatically input the respiratory condition into the nursing record (vital record) and display the same, and it is possible to automatically transmit information on the deterioration of the respiratory condition to the nurse. Therefore, it is possible to decrease the number of times of the checking for the patient at night by the nurse, it is possible to decrease the amount of work of the nurse, and it is possible to improve the quality of the sleep of the patient. Further, for example, when the falling from the bed, the respiratory arrest, the cardiac arrest, or the death, which is not anticipated by the medical staff, occurs, the biometric information monitoring system of one aspect of the present disclosure can be also utilized to investigate the cause thereof.

Further, the present invention can be described in accordance with the following items:

Item 1. A biometric (biological) information monitoring system for monitoring biometric (biological) information of a subject on a bed, the system comprising:

a plurality of load detectors which are placed in the bed or under feet of the bed and which detect a load of the subject;

a center of gravity position calculating unit which acquires a temporal variation of a center of gravity position of the subject based on the detected load of the subject;

a body motion information determining unit which acquires information on a body motion of the subject based on the acquired temporal variation of the center of gravity position of the subject; and a respiratory rate calculating unit which calculates a respiratory rate of the subject based on the acquired temporal variation of the center of gravity position of the subject and the information on the body motion of the subject acquired by the body motion information determining unit.

Item 2. The biometric information monitoring system according to item 1, wherein the body motion information determining unit includes a first body motion information determining unit which determines information on a large body motion of the subject and a second body motion information determining unit which determines information on a small body motion of the subject.

Item 3. The biometric information monitoring system according to item 2, wherein the first body motion information determining unit determines a variation caused by the large body motion of the subject included in the temporal variation of the center of gravity position of the subject, based on a movement distance of the center of gravity position within a predetermined time period.

Item 4. The biometric information monitoring system according to item 2 or 3, wherein the second body motion information determining unit determines a variation, caused by the small body motion of the subject, included in the temporal variation of the center of gravity position of the subject, based on a movement direction of the center of gravity position, the temporal variation of the center of gravity position being a variation from which the variation caused by the large body motion determined by the first body motion information determining unit has been removed.

Item 5. The biometric information monitoring system according to any one of items 2 to 4, wherein the respiratory rate calculating unit calculates the respiratory rate based on the temporal variation of the center of gravity position of the subject from which the variation caused by the large body motion determined by the first body motion information determining unit and the variation caused by the small body motion determined by the second body motion information determining unit have been removed.

Item 6. The biometric information monitoring system according to any one of items 2 to 4, wherein the information on the large body motion, the information on the small body motion, and the respiratory rate are synchronously acquired.

Item 7. The biometric information monitoring system according to any one of items 1 to 6, further comprising a physical condition judging unit which judges whether the subject is in a sleep state or a wakeful state based on the acquired information on the body motion of the subject and/or the respiratory rate of the subject.

Item 8. The biometric information monitoring system according to item 7, further comprising:
a bed-leaving/settling judging unit which judges whether or not the subject is present on the bed based on the detected load, wherein:
the physical condition judging unit judges that the subject has fallen from the bed in a case that the subject is judged to be in the sleep state by the physical condition judging unit and is judged to have left the bed by the bed-leaving/settling judging unit.

Item 9. The biometric information monitoring system according to any one of items 1 to 8, further comprising a heart rate calculating unit which acquires a heart rate of the subject based on the acquired temporal variation of the center of gravity position of the subject.

Item 10. The biometric information monitoring system according to item 9, wherein the physical condition judging unit judges whether the subject is alive or dead based on the acquired information on the body motion, the respiratory rate, and the heart rate of the subject.

Item 11. The biometric information monitoring system according to any one of items 1 to 10, further comprising a display unit which displays a temporal variation of the acquired information on the body motion of the subject as a history of movement of the center of gravity position on the bed.

Item 12. The biometric information monitoring system according to any one of items 1 to 11, further comprising a notifying unit which performs notification based on the acquired temporal variation of the center of gravity position of the subject.

Item 13. The biometric information monitoring system according to any one of items 1 to 12, wherein the temporal variation of the center of gravity position includes a variation caused by a body motion of the subject and a variation caused by a respiration of the subject, and the biometric information monitoring system further comprises a body axis determining unit which acquires a body axis of the subject based on the variation caused by the respiration.

Item 14. The biometric information monitoring system according to any one of items 1 to 13, further comprising a body weight measuring unit which acquires a body weight of the subject based on the detected load.

Item 15. A bed system comprising:
a bed; and
the biometric information monitoring system as defined in any one of items 1 to 14.

The invention claimed is:

1. A biological information monitoring system for monitoring biological information of a subject on a bed, the system comprising:
a plurality of load detectors which are configured to be placed in the bed or under feet of the bed and which detect a load of the subject; and
a controller configured to control the biological information monitoring system,
wherein the controller is configured to control the biological information monitoring system to:
acquire a temporal variation of a center of gravity position of the subject based on the detected load of the subject;
acquire information on a body motion of the subject based on the acquired temporal variation of the center of gravity position of the subject; and
calculate a respiratory rate of the subject based on the acquired temporal variation of the center of gravity position of the subject and the information on the body motion of the subject,
wherein the body motion information is an information on a movement of a whole body or a part of the whole body of the subject, the movement being different from a movement caused by a respiration of the subject;
the body motion information includes an information on a large body motion of the subject and an information on a small body motion of the subject, an amount of movement of the center of gravity position of the subject within a predetermined time period caused by the small body motion being smaller than an amount of movement of the center of gravity position of the subject within the predetermined time period caused by the large body motion;
the acquiring of the information on the body motion of the subject includes determining a variation caused by the large body motion of the subject included in the temporal variation of the center of gravity position of the subject, based on a movement distance of the center of gravity position within a predetermined time period; and
determining a variation, caused by the small body motion of the subject, included in the temporal variation of the center of gravity position of the subject, based on a movement direction of the center of gravity position by first identifying a movement direction of the center of gravity position caused by the respiration of the subject and then comparing the movement direction of the center of gravity position with the movement direction of the center of gravity position caused by the respiration of the subject,
wherein the calculating of the respiratory rate of the subject includes removing the determined variation caused by the large body motion and the determined variation caused by the small body motion from the temporal variation of the center of gravity position; and
calculating the respiratory rate of the subject based on an oscillation of the center of gravity position of the subject caused by the respiration of the subject.

2. The biological information monitoring system according to claim 1, wherein the information on the large body motion, the information on the small body motion, and the respiratory rate are synchronously acquired.

3. The biological information monitoring system according to claim 1, wherein the controller is further configured to control the biological information monitoring system to judge whether the subject is in a sleep state or a wakeful state based on the acquired information on the body motion of the subject and/or the respiratory rate of the subject.

4. The biological information monitoring system according to claim 3, wherein the controller is further configured to control the biological information monitoring system to:
judge whether or not the subject is present on the bed based on the detected load, and
judge that the subject has fallen from the bed in a case that the subject is judged to be in the sleep state and is judged to have left the bed.

5. The biological information monitoring system according to claim 1, wherein the controller is further configured to control the biological information monitoring system to acquire a heart rate of the subject based on the acquired temporal variation of the center of gravity position of the subject.

6. The biological information monitoring system according to claim 5, wherein the controller is further configured to control the biological information monitoring system to judge whether the subject is alive or dead based on the acquired information on the body motion, the respiratory rate, and the heart rate of the subject.

7. The biological information monitoring system according to claim 1, further comprising a display which displays a temporal variation of the acquired information on the body motion of the subject as a history of movement of the center of gravity position on the bed.

8. The biological information monitoring system according to claim 1, wherein the controller is further configured to control the biological information monitoring system to perform notification based on the acquired temporal variation of the center of gravity position of the subject.

9. The biological information monitoring system according to claim 1, wherein the controller is further configured to control the biological information monitoring system to acquire a body weight of the subject based on the detected load.

10. A bed system comprising:
a bed; and
the biological information monitoring system as defined in claim 1.

11. A biological information monitoring system for monitoring biological information of a subject on a bed, the system comprising:
a plurality of load detectors which are configured to be placed under feet of the bed and which detect a load of the subject; and
a controller configured to control the biological information monitoring apparatus,
wherein the controller is configured to control the biological information monitoring system to:
acquire a temporal variation of a center of gravity position of the subject based on the detected load of the subject;
acquire information on a body motion of the subject based on the acquired temporal variation of the center of gravity position of the subject; and
calculate a respiratory rate of the subject based on the acquired temporal variation of the center of gravity position of the subject and the information on the body motion of the subject,
wherein the body motion information is an information on a movement of a whole body or a part of the whole body of the subject, the movement being different from a movement caused by a respiration of the subject;
the temporal variation of the center of gravity position includes a variation caused by a body motion of the subject and a variation caused by a respiration of the subject; and
the controller is further configured to control the biological information monitoring system to determine that a direction of an oscillation of the center of gravity position of the subject caused by the respiration of the subject is an extending direction of a backbone of the subject.

12. The biological information monitoring system according to claim 11, wherein the controller is further configured to control the biological information monitoring system to judge whether the subject is in a sleep state or a wakeful state based on the acquired information on the body motion of the subject and/or the respiratory rate of the subject.

13. The biological information monitoring system according to claim 12, wherein the controller is further configured to control the biological information monitoring system to:
judge whether or not the subject is present on the bed based on the detected load, and
judge that the subject has fallen from the bed in a case that the subject is judged to be in the sleep state and is judged to have left the bed.

14. The biological information monitoring system according to claim 11, wherein the controller is further configured to control the biological information monitoring system to acquire a heart rate of the subject based on the acquired temporal variation of the center of gravity position of the subject.

15. The biological information monitoring system according to claim 14, wherein the controller is further configured to control the biological information monitoring system to judge whether the subject is alive or dead based on the acquired information on the body motion, the respiratory rate, and the heart rate of the subject.

16. The biological information monitoring system according to claim 11, further comprising a display which displays a temporal variation of the acquired information on the body motion of the subject as a history of movement of the center of gravity position on the bed.

17. The biological information monitoring system according to claim 11, wherein the controller is further configured to control the biological information monitoring system to perform notification based on the acquired temporal variation of the center of gravity position of the subject.

18. The biological information monitoring system according to claim 11, wherein the controller is further configured to control the biological information monitoring system to acquire a body weight of the subject based on the detected load.

19. A bed system comprising:
a bed; and
the biological information monitoring system as defined in claim 11.

20. A biological information monitoring method for monitoring biological information of a subject on a bed, the method comprising:
detecting a load of the subject by a plurality of load detectors placed in the bed or under feet of the bed;
acquiring a temporal variation of a center of gravity position of the subject based on the detected load of the subject;

acquiring information on a body motion of the subject based on the acquired temporal variation of the center of gravity position of the subject; and calculating a respiratory rate of the subject based on the acquired temporal variation of the center of gravity position of the subject and the information on the body motion of the subject, wherein the body motion information is an information on a movement of a whole body or a part of the whole body of the subject, the movement being different from a movement caused by a respiration of the subject;

wherein the body motion information includes an information on a large body motion of the subject and an information on a small body motion of the subject, an amount of movement of the center of gravity position of the subject within a predetermined time period caused by the small body motion being smaller than an amount of movement of the center of gravity position of the subject within the predetermined time period caused by the large body motion;

wherein the acquiring of the information on the body motion of the subject includes determining a variation caused by the large body motion of the subject included in the temporal variation of the center of gravity position of the subject, based on a movement distance of the center of gravity position within a predetermined time period, and determining a variation, caused by the small body motion of the subject, included in the temporal variation of the center of gravity position of the subject, based on a movement direction of the center of gravity position by first identifying a movement direction of the center of gravity position caused by the respiration of the subject and then comparing the movement direction of the center of gravity position with the movement direction of the center of gravity position caused by the respiration of the subject; and wherein the calculating of the respiratory rate of the subject includes removing the determined variation caused by the large body motion and the determined variation caused by the small body motion from the temporal variation of the center of gravity position, and calculating the respiratory rate of the subject based on an oscillation of the center of gravity position of the subject caused by the respiration of the subject.

21. A biological information monitoring method for monitoring biological information of a subject on a bed, the method comprising:

detecting a load of the subject by a plurality of load detectors placed under feet of the bed;

acquiring a temporal variation of a center of gravity position of the subject based on the detected load of the subject;

acquiring information on a body motion of the subject based on the acquired temporal variation of the center of gravity position of the subject; and calculating a respiratory rate of the subject based on the acquired temporal variation of the center of gravity position of the subject and the information on the body motion of the subject, wherein the body motion information is an information on a movement of a whole body or a part of the whole body of the subject, the movement being different from a movement caused by a respiration of the subject; and wherein the temporal variation of the center of gravity position includes a variation caused by a body motion of the subject and a variation caused by a respiration of the subject;

the method further comprising determining that a direction of an oscillation of the center of gravity position of the subject caused by the respiration of the subject is an extending direction of a backbone of the subject.

* * * * *